US012728275B2

(12) United States Patent
Prutchi et al.

(10) Patent No.: US 12,728,275 B2
(45) Date of Patent: Sep. 8, 2026

(54) COMBINED IMPLANTABLE PULSE GENERATOR DEVICE

(71) Applicant: Impulse Dynamics NV, Willemstad (CW)

(72) Inventors: David Prutchi, Voorhees, NJ (US); Jason Meyers, Haddonfield, NJ (US); Tamir Ben David, Tel-Aviv (IL)

(73) Assignee: Impulse Dynamics NV, Willemstad (CW)

( * ) Notice: Subject to any disclaimer, the term of this patent is extended or adjusted under 35 U.S.C. 154(b) by 182 days.

(21) Appl. No.: 18/266,334

(22) PCT Filed: Dec. 13, 2021

(86) PCT No.: PCT/IB2021/061650
§ 371 (c)(1),
(2) Date: Jun. 9, 2023

(87) PCT Pub. No.: WO2022/123547
PCT Pub. Date: Jun. 16, 2022

(65) Prior Publication Data

US 2024/0100349 A1 Mar. 28, 2024

Related U.S. Application Data

(60) Provisional application No. 63/124,824, filed on Dec. 13, 2020.

(51) Int. Cl.
*A61N 1/39* (2006.01)
*A61N 1/05* (2006.01)
(Continued)

(52) U.S. Cl.
CPC ....... *A61N 1/39622* (2017.08); *A61N 1/0563* (2013.01); *A61N 1/36585* (2013.01); *A61N 1/3702* (2013.01); *G16H 20/30* (2018.01)

(58) Field of Classification Search
CPC .............. A61N 1/3702; A61N 1/36585; A61N 1/39622
See application file for complete search history.

(56) References Cited

U.S. PATENT DOCUMENTS 8,311,629 B2 11/2012 Ben-Haim et al.
8,321,013 B2 11/2012 Darvish et al.
(Continued)

FOREIGN PATENT DOCUMENTS

CN 105102060 11/2015
JP 2012-502729 2/2012
(Continued)

OTHER PUBLICATIONS

International Preliminary Report on Patentability Dated Jun. 22, 2023 From the International Bureau of WIPO Re. Application No. PCT/IB2021/061650 (12 Pages).
(Continued)

*Primary Examiner* — William J Levicky

(57) ABSTRACT

A method of treating a heart, the method including providing an Implantable Pulse Generator (IPG) adapted to provide a combination of at least two treatment modalities including Cardiac Contractility Modulation therapy and one more modality selected from a group consisting of Cardiac pacing, Cardioversion, Defibrillation, Cardioversion and Defibrillation, and Cardiac Resynchronization Therapy (CRT), detecting a patient's physical condition, and selecting a combination of Cardiac Contractility Modulation therapy and at least one treatment modality from the group, and providing the combination of the Cardiac Contractility Modulation therapy and the at least one treatment modality. Related apparatus and methods are also described.

24 Claims, 13 Drawing Sheets

(51) Int. Cl.

| | |
|---|---|
| ***A61N 1/365*** | (2006.01) |
| ***A61N 1/37*** | (2006.01) |
| ***G16H 20/30*** | (2018.01) |

(56) References Cited

U.S. PATENT DOCUMENTS

| | | | | |
|---|---|---|---|---|
| 8,560,067 | B2 | 10/2013 | Salo et al. | |
| 8,706,230 | B2 | 4/2014 | Rousso et al. | |
| 8,958,872 | B2 | 2/2015 | Ben-Haim et al. | |
| 9,265,950 | B2 | 2/2016 | Zhu et al. | |
| 9,320,886 | B2 | 4/2016 | Rousso et al. | |
| 9,333,364 | B2 | 5/2016 | Echt et al. | |
| 9,956,390 | B2 | 5/2018 | Rousso et al. | |
| 2009/0099618 | A1* | 4/2009 | Rousso ................ | A61N 1/3627 607/9 |
| 2010/0069977 | A1 | 3/2010 | Stahmann | |
| 2010/0069985 | A1* | 3/2010 | Stahmann ............ | A61N 1/3627 607/9 |
| 2013/0006318 | A1 | 1/2013 | Weiss et al. | |
| 2013/0006319 | A1 | 1/2013 | Doerr | |

FOREIGN PATENT DOCUMENTS

| | | |
|---|---|---|
| WO | WO 2021/079319 | 4/2021 |
| WO | WO 2022/123547 | 6/2022 |

OTHER PUBLICATIONS

International Search Report and the Written Opinion Dated May 23, 2022 From the International Searching Authority Re. Application No. PCT/IB2021/061650. (20 Pages).

Swenson et al. "Direct Comparison of A Novel Antitachycardia Pacing Algorithm Against Present Methods Using Virtual Patient Modeling", Heart Rhythm, 17(9): 1602-1608, Sep. 2020.

Communication Pursuant to Article 94(3) EPC Dated Mar. 21, 2025 From the European Patent Office Re. Application No. 21873685.8 (7 Pages).

Notice of Reason(s) for Rejection Dated Sep. 9, 2025 From the Japan Patent Office Re. Application No. 2023-535050 and Its Translation Into English. (5 Pages).

Relatório de Busca e Parecer [Search Reportand Opinion] Dated Mar. 11, 2026 From the Serviço Público Federal, Ministério da Economia, Instituto Nacional da Propriedade Industrial do Brasil Re. Application No. BR 11 2023 007392 8 and Its Translation Into English. (8 Pages).

Notification of Office Action and Search Report Dated May 16, 2026 From the State Intellectual Property Office of the People's Republic of China Re. Application No. 2021180083763.5 and Its Machine Translation Into English. (17 Pages).

Communication Pursuant to Article 94(3) EPC Dated Jul. 2, 2026 From the European Patent Office Re. Application No. 21873685.8 (6 Pages).

* cited by examiner

PROVIDING AN IMPLANTABLE PULSE GENERATOR (IPG) ADAPTED TO PROVIDE A COMBINATION OF AT LEAST TWO TREATMENT MODALITIES INCLUDING CARDIAC CONTRACTILITY MODULATION THERAPY AND ONE MORE MODALITY SELECTED FROM :

454

CARDIAC PACING;

CARDIOVERSION

CARDIOVERSION AND DEFIBRILLATION

CARDIAC RESYNCHRONIZATION THERAPY (CRT)

452

PROVIDE DEFIBRILLATION TREATMENT 402

PROVIDE CCM TREATMENT 404

PROVIDE DEFIBRILLATION TREATMENT 412

SUPPRESS CCM TREATMENT 414

STOP CONDITION REACHED? 416

NO

YES

SUPPRESS CCM TREATMENT 418

COMBINED IMPLANTABLE PULSE GENERATOR DEVICE

RELATED APPLICATIONS

This application is a National Phase of PCT Patent Application No. PCT/IB2021/061650 having International filing date of Dec. 13, 2021 which is a Continuation-In-Part of and claims the benefit of priority under 35 USC § 119(e) of U.S. Provisional Patent Application No. 63/124,824 filed on Dec. 13, 2020.

PCT Patent Application No. PCT/IB2021/061650 is also related to U.S. Provisional Patent Application No. 62/957,243 filed on Jan. 5, 2020.

The contents of the above applications are all incorporated by reference as if fully set forth herein in their entirety.

FIELD AND BACKGROUND OF THE INVENTION

The present invention, in some embodiments thereof, relates to an Implantable Pulse Generator (IPG) device and, more particularly, but not exclusively, to methods of operating an IPG.

Additional background art includes:

U.S. Pat. No. 8,311,629 to Ben Haim et al.

The disclosures of all references mentioned above and throughout the present specification, as well as the disclosures of all references mentioned in those references, are hereby incorporated herein by reference.

SUMMARY OF THE INVENTION

The present invention, in some embodiments thereof, relates to an Implantable Pulse Generator (IPG) device and, more particularly, but not exclusively, to methods of operating an IPG.

An aspect of some embodiments includes a device packaging together one or more of the following cardiac treatments: Cardiac Contractility Modulation, Cardioversion, Defibrillation, Cardiac Pacing and Cardiac Resynchronization Therapy (CRT).

An aspect of some embodiments includes methods of treatment of one or more of the above-mentioned treatments in combination with at least one other of the above-mentioned treatments.

According to an aspect of some embodiments of the present disclosure there is provided an Implantable Pulse Generator (IPG) including Cardiac Contractility Modulation generator circuitry adapted to provide a Cardiac Contractility Modulation treatment modality, pacing generator circuitry adapted to provide a cardiac pacing treatment modality, Cardioversion generator circuitry adapted to provide a Cardioversion treatment modality, defibrillation pulse generator circuitry adapted to provide a Defibrillation treatment modality, such as implantable cardioverter defibrillation (ICD), Cardiac Resynchronization Therapy (CRT) generator circuitry adapted to provide a Cardiac Resynchronization Therapy (CRT) treatment modality, and a controller adapted to gather cardiac data to evaluate clinical benefit of providing at least one of the treatment modalities over an evaluation period, wherein the IPG is enabled to determine the clinical benefit by comparing at least some of the cardiac data to reference data included in the IPG.

According to some embodiments of the disclosure, the IPG includes storage for storing a value of the clinical benefit.

According to some embodiments of the disclosure, the controller is enabled to automatically provide a specific treatment modality based on the clinical benefit.

According to some embodiments of the disclosure, the controller is adapted to record decisions associated with one or more of the Cardiac Contractility Modulation generator circuitry, the pacing generator circuitry, the Cardioversion generator circuitry, the defibrillation pulse generator circuitry, and the CRT generator circuitry, even when the circuitries do not provide pulse activation.

According to some embodiments of the disclosure, the controller is adapted detect a decline in clinical benefit of a treatment modality.

According to some embodiments of the disclosure, the controller is adapted to provide a combination of ICD and CRT treatment modalities if providing the Cardiac Contractility Modulation treatment modality has not provided clinical benefit over the evaluation period.

According to some embodiments of the disclosure, the controller is adapted to provide a combination of ICD and Cardiac Contractility Modulation treatment modalities if providing the CRT treatment modality has not provided clinical benefit over the evaluation period.

According to some embodiments of the disclosure, the controller is adapted to provide a combination of ICD, Cardiac Contractility Modulation, and CRT treatment modalities if providing the Cardiac Contractility Modulation and CRT treatment modalities have provided clinical benefit over the evaluation period.

According to some embodiments of the disclosure, the controller is programmable to provide a series of treatment modalities and combinations of treatment modalities, measure cardiac parameters during evaluation periods associated with the treatment modalities, compare the cardiac parameters associated with the treatment modalities, and select a treatment modality or combination of treatment modalities based on the patient's cardiac parameters obtained during the series.

According to some embodiments of the disclosure, the IPG is configured to measure one or more cardiac parameter(s) selected from a group consisting of a level of ventricle arrhythmia, a level of atrial arrhythmia, a duration of a QRS complex, cardiac output (CO), stroke volume (SV), and end diastolic volume (EDV), and store data associated with the cardiac parameter over an evaluation period.

According to some embodiments of the disclosure, the evaluation period is at least one month.

According to some embodiments of the disclosure, the controller is adapted to provide ICD treatment modality if level of ventricular arrhythmia exceed a ventricular arrhythmia threshold.

According to some embodiments of the disclosure, the controller is adapted to provide CRT treatment modality if duration of QRS complex exceeds a QRS duration threshold.

According to some embodiments of the disclosure, the controller is adapted to provide Cardiac Contractility Modulation treatment modality if SV/EDV ratio is below an SV/EDV ratio threshold.

According to some embodiments of the disclosure, the controller is adapted to control the IPG and the generator circuitry to switch between providing one of the treatment modalities and another of the treatment modalities.

According to some embodiments of the disclosure, the IPG includes leads sized for reaching locations where the treatment modalities are to be provided.

According to some embodiments of the disclosure, the IPG is adapted to select which two of the treatment modalities is to be provided.

According to some embodiments of the disclosure, the IPG is adapted to select providing Cardiac Contractility Modulation and one other of the treatment modalities.

According to some embodiments of the disclosure, the IPG is adapted to provide all of the treatment modalities.

According to some embodiments of the disclosure, the IPG including a first lead for providing Cardiac Contractility Modulation therapy, a second lead for providing Cardiac Contractility Modulation therapy, and a therapy controller adapted to control provide Contractility Modulation therapy via the first lead and the second lead within a same heartbeat, wherein the device is adapted to provide a different pattern of Cardiac Contractility Modulation pulses via the first lead than via the second lead.

According to some embodiments of the disclosure, the IPG including a first lead shaped and configured for providing Cardiac Contractility Modulation therapy to a right ventricle, a second lead shaped and configured for providing Cardiac Contractility Modulation therapy to the right ventricle, a third lead shaped for placing in a right atrium, and a controller adapted to switch providing between at least two treatment modalities selected from a group consisting of Cardiac Contractility Modulation, Cardiac pacing, Cardioversion, Defibrillation, Cardioversion and Defibrillation, and Cardiac Resynchronization Therapy (CRT), the controller adapted to control provide Contractility Modulation therapy via the first lead and the second lead within a same heartbeat.

According to some embodiments of the disclosure, at least one of the leads includes a shock coil and a pacing electrode in the lead.

According to some embodiments of the disclosure, the device is adapted to provide a pacing signal through the first lead to the right ventricle and through the third lead to the right atrium within a same heartbeat.

According to an aspect of some embodiments of the present disclosure there is provided an Implantable Pulse Generator (IPG) device for providing Cardiac Contractility Modulation therapy, the IPG including a first lead for providing Cardiac Contractility Modulation therapy, a second lead for providing Cardiac Contractility Modulation therapy, and a therapy controller adapted to control provide Contractility Modulation therapy via the first lead and the second lead within a same heartbeat, wherein the device is adapted to provide a different pattern of Cardiac Contractility Modulation pulses via the first lead than via the second lead.

According to an aspect of some embodiments of the present disclosure there is provided a method of selecting a treatment or combination of treatments, the method including programming an IPG to provide a series of treatments and combinations of treatments, the IPG measuring cardiac parameters during evaluation periods associated with the treatments, comparing the cardiac parameters associated with the treatments, and selecting a treatment or combination of treatments based on the patient's cardiac parameters obtained during the series.

According to some embodiments of the disclosure, the comparing is performed by the IPG.

According to some embodiments of the disclosure, the selecting is performed by the IPG.

According to an aspect of some embodiments of the present disclosure there is provided a method of treating a heart, the method including providing an Implantable Pulse Generator (IPG) adapted to provide a combination of at least two treatment modalities including Cardiac Contractility Modulation therapy and one more modality selected from a group consisting of Cardiac pacing, Cardioversion, Defibrillation, Cardioversion and Defibrillation, and Cardiac Resynchronization Therapy (CRT), detecting a patient's physical condition, and selecting a combination of Cardiac Contractility Modulation therapy and at least one treatment modality from the group, and providing the combination of the Cardiac Contractility Modulation therapy and the at least one treatment modality.

According to some embodiments of the disclosure, providing the combination includes refraining from providing Cardiac Contractility Modulation therapy during a cardiac cycle when the at least one treatment modality is provided.

According to some embodiments of the disclosure, providing the combination includes refraining from providing Cardiac Contractility Modulation therapy during a cardiac cycle when the at least one treatment modality is provided based on the detecting.

According to some embodiments of the disclosure, the detecting the patient's physical condition includes a physician detecting the patient's physical condition.

According to some embodiments of the disclosure, the detecting the patient's physical condition is based on a clinical parameter based on analysis of a physiological measure selected from a group consisting of blood pressure, an electrocardiogram (ECG) signal, breathing rate, ejection fraction, arrhythmia, bio impedance, a blood test, cardiac imaging, physical examination, and biopsy.

According to some embodiments of the disclosure, the detecting the patient's physical condition includes using clinical parameters provided by a physician.

According to some embodiments of the disclosure, the detecting the patient's physical condition includes using data provided by sensors included in the IPG.

According to some embodiments of the disclosure, the detecting the patient's physical condition includes using data provided by sensors external to a patient's body.

According to some embodiments of the disclosure, the providing the Cardiac Contractility Modulation treatment includes providing an increased dose of Cardiac Contractility Modulation treatment following providing cardioversion treatment.

According to some embodiments of the disclosure, the providing the Cardiac Contractility Modulation treatment includes providing an increased dose of Cardiac Contractility Modulation treatment following providing defibrillation treatment.

According to some embodiments of the disclosure, the IPG is used for providing defibrillation treatment, and following the providing defibrillation treatment, refraining from providing Cardiac Contractility Modulation treatment until an arrhythmia rate is below a specific threshold.

According to some embodiments of the disclosure, the specific threshold of the arrhythmia rate is pre-programmed in the IPG.

According to some embodiments of the disclosure, the specific threshold of the arrhythmia rate is 1 arrhythmia event per 1 minute.

According to some embodiments of the disclosure, a sensor in the IPG is used to determine the arrhythmia rate.

According to some embodiments of the disclosure, the IPG is used to provide defibrillation treatment, and following the providing defibrillation treatment, refraining from providing Cardiac Contractility Modulation treatment for a pre-programmed time period.

According to some embodiments of the disclosure, the time period is in a range from 1 to 90 days.

According to some embodiments of the disclosure, the IPG is used to provide Cardiac Contractility Modulation treatment during cardiac cycles when CRT pacing is not provided.

According to some embodiments of the disclosure, the IPG is used to provide Cardiac Contractility Modulation treatment in a same cardiac cycle as CRT pacing is provided.

According to some embodiments of the disclosure, the IPG is used to provide Cardiac Contractility Modulation treatment only in a cardiac cycle triggered by a pacemaker or CRT pulse.

According to some embodiments of the disclosure, the IPG is used to provide Cardiac Contractility Modulation treatment only in a cardiac cycle which is not triggered by a pacemaker or CRT pulse.

According to some embodiments of the disclosure, the IPG is used to provide Cardiac Contractility Modulation treatment only when a heart rate is determined to be in a specific range.

According to an aspect of some embodiments of the present disclosure there is provided an Implantable Pulse Generator (IPG) including Cardiac Contractility Modulation generator circuitry adapted to provide a Cardiac Contractility Modulation treatment modality, pacing generator circuitry adapted to provide a cardiac pacing treatment modality, Cardioversion generator circuitry adapted to provide a Cardioversion treatment modality, defibrillation pulse generator circuitry adapted to provide a Defibrillation treatment modality, Cardiac Resynchronization Therapy (CRT) generator circuitry adapted to provide a CRT treatment modality, and a controller adapted to control the IPG and the generator circuitry to switch between providing one of the treatment modalities and another of the treatment modalities.

According to some embodiments of the disclosure, at least some of the treatment modality generator circuitries are separate circuits.

According to some embodiments of the disclosure, the IPG includes leads sized for reaching locations where the treatment modalities are to be provided.

According to some embodiments of the disclosure, the IPG is adapted to provide all of the treatment modalities.

According to an aspect of some embodiments of the present disclosure there is provided an Implantable Pulse Generator (IPG) including Cardiac Contractility Modulation generator circuitry adapted to provide a Cardiac Contractility Modulation treatment modality, pacing generator circuitry adapted to provide a cardiac pacing treatment modality, Cardioversion generator circuitry adapted to provide a Cardioversion treatment modality, defibrillation pulse generator circuitry adapted to provide a Defibrillation treatment modality, Cardiac Resynchronization Therapy (CRT) generator circuitry adapted to provide a Cardiac Resynchronization Therapy (CRT) treatment modality, and a controller adapted to control the generator circuitry thereby selecting which one of the treatment modalities of the treatment modalities is to be provided.

According to some embodiments of the disclosure, at least some of the treatment modality generator circuitries are separate circuits.

According to some embodiments of the disclosure, the IPG is adapted to select which two of the treatment modalities is to be provided.

According to some embodiments of the disclosure, the IPG is adapted to select which two of the treatment modalities is to be provided within a same heartbeat.

According to some embodiments of the disclosure, the IPG is adapted to select providing Cardiac Contractility Modulation and one other of the treatment modalities.

According to an aspect of some embodiments of the present disclosure there is provided a method of implanting an Implantable Pulse Generator (IPG) and selecting a preferred treatment modality the method including implanting an IPG with Cardiac Contractility Modulation and at least one additional stimulation modality, selecting a preferred treatment modality or modalities, periodically checking if modality or modalities selection is correct for a patient, if the modality or modalities selection is correct, then continue periodically checking, else return to selecting a preferred treatment modality or modalities.

According to an aspect of some embodiments of the present disclosure there is provided an Implantable Pulse Generator (IPG) device for providing Cardiac Contractility Modulation therapy, the IPG including a first lead shaped and configured for providing Cardiac Contractility Modulation therapy to a right ventricle, a second lead shaped and configured for providing Cardiac Contractility Modulation therapy to the right ventricle, a third lead shaped for placing in a right atrium, and a controller adapted to switch providing between at least two treatment modalities selected from a group consisting of Cardiac Contractility Modulation, Cardiac pacing, Cardioversion, Defibrillation, Cardioversion and Defibrillation, and Cardiac Resynchronization Therapy (CRT), the controller adapted to control provide Contractility Modulation therapy via the first lead and the second lead within a same heartbeat.

According to some embodiments of the disclosure, the device includes a fourth lead shaped for placing in a left ventricle.

According to some embodiments of the disclosure, a at least one of the leads includes a shock coil and a pacing electrode in the lead.

According to some embodiments of the disclosure, the device is adapted to provide a pacing signal through the first lead to the right ventricle and through the third lead to the right atrium within a same heartbeat.

According to an aspect of some embodiments of the present disclosure there is provided a method of adding a cardiac treatment modality to an Implantable Pulse Generator (IPG), the method including adding programming for providing an additional cardiac treatment modality to a controller in an IPG which already has programming for providing a cardiac treatment modality, and connecting an additional lead associated with the additional cardiac treatment modality to the IPG.

According to some embodiments of the disclosure, the IPG is implanted in a patient, and the connecting the additional lead associated with the additional cardiac treatment modality includes implanting the additional lead.

According to an aspect of some embodiments of the present disclosure there is provided a method of providing Cardiac Contractility Modulation therapy, the method including alternately providing one bi-phasic Cardiac Contractility Modulation pulse at a time via a first lead and a second lead within the same heartbeat.

According to some embodiments of the disclosure, the providing Cardiac Contractility Modulation therapy via the first lead followed by providing Cardiac Contractility Modulation therapy via the second lead includes a time delay between the providing via the first lead and the providing via the second lead.

According to some embodiments of the disclosure, an amplitude of a Cardiac Contractility Modulation pulse via the first lead is not equal to an amplitude of the Cardiac Contractility Modulation pulse via the second lead.

According to some embodiments of the disclosure, an interval between a positive and a negative phase of the bi-phasic Cardiac Contractility Modulation pulse via the first lead is not equal to an interval between a positive and a negative phase of the bi-phasic Cardiac Contractility Modulation pulse via the second lead.

According to an aspect of some embodiments of the present disclosure there is provided an Implantable Pulse Generator (IPG) device for providing Cardiac Contractility Modulation therapy, the IPG including a first lead for providing Cardiac Contractility Modulation therapy, a second lead for providing Cardiac Contractility Modulation therapy, and a therapy controller adapted to control provide Contractility Modulation therapy via the first lead and the second lead within a same heartbeat, wherein the device is adapted to provide a different pattern of Cardiac Contractility Modulation pulses via the first lead than via the second lead.

According to an aspect of some embodiments of the present disclosure there is provided a method of providing cardiac therapy, the method including providing Cardiac Contractility Modulation therapy, receiving a control signal to provide cardioversion treatment, and based on receiving the signal, stopping the Cardiac Contractility Modulation therapy and providing cardioversion treatment.

According to an aspect of some embodiments of the present disclosure there is provided a method of providing cardiac therapy, the method including providing Cardiac Contractility Modulation treatment, receiving a control signal to provide defibrillation, and based on receiving the signal, stopping the Cardiac Contractility Modulation therapy and providing defibrillation treatment.

According to an aspect of some embodiments of the present disclosure there is provided a method of providing cardiac therapy, the method including providing Cardiac Resynchronization Therapy (CRT), receiving a control signal to provide Cardiac Contractility Modulation therapy, and providing Cardiac Contractility Modulation therapy.

According to some embodiments of the disclosure, providing Cardiac Contractility Modulation therapy is only during cardiac cycles when CRT is not provided.

According to some embodiments of the disclosure, the providing Cardiac Contractility Modulation therapy only during cardiac cycles when CRT is not provided is controlled by a controller included in an Implantable Pulse Generator (IPG) refraining from providing Cardiac Contractility Modulation therapy during a cardiac cycle when the IPG provides CRT.

According to some embodiments of the disclosure, providing Cardiac Contractility Modulation therapy is performed during a same cardiac cycle as providing CRT.

According to some embodiments of the disclosure, a Cardiac Contractility Modulation therapy signal is used to provide CRT.

According to some embodiments of the disclosure, the providing Cardiac Contractility Modulation therapy during a same cardiac cycle as providing CRT is controlled based on an Implantable Pulse Generator (IPG) timing the providing Cardiac Contractility Modulation therapy a specific period of time following when the IPG provides the CRT.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as one of the above-mentioned treatments, might be expected to use completely different methods, e.g., making use of expert knowledge and/or the pattern recognition capabilities of the human brain, which might be different, or even vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1A:
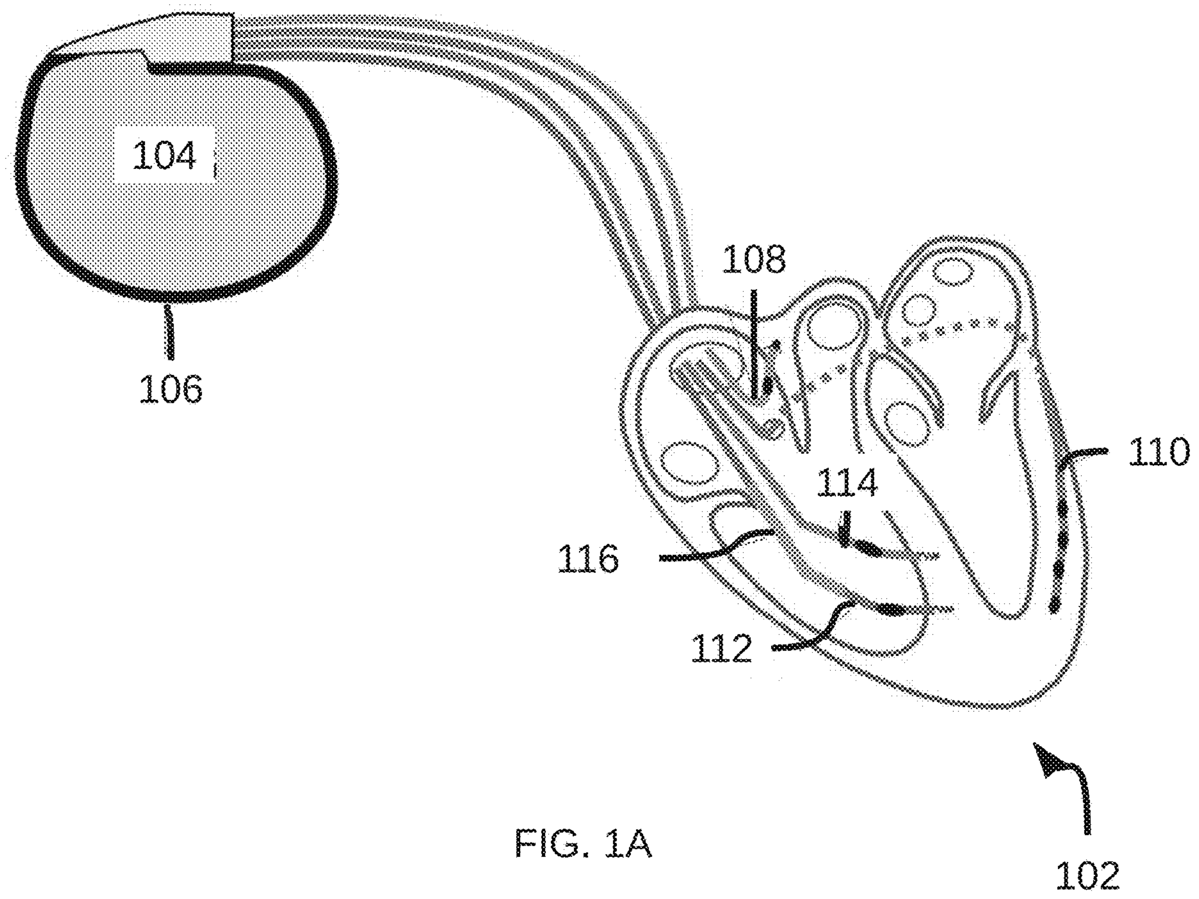
FIG. 1A is a simplified illustration showing an IPG and leads placed in a heart.

The present invention, in some embodiments thereof, relates to an Implantable Pulse Generator (IPG) device and, more particularly, but not exclusively, to methods of operating an IPG.

Introduction

An aspect of some embodiments relates to packaging several treatment capabilities in one Implantable Pulse Generator (IPG) device.

Current Cardiac Contractility Modulation treatment is given using a standalone device that provides Cardiac Contractility Modulation stimulation to the heart ventricle/s, and may have a sensing electrode in the right atrium.

Patients that needs both Cardiac Contractility Modulation and other cardiac stimulation therapies will get at least two separate implantable devices, one for Cardiac Contractility Modulation and one or more for other therapies.

In some embodiments, a combined implantable pulse generator (IPG) device is described, which provides a Cardiac Contractility Modulation treatment modality and at least one additional modality, such as by way of some non-limiting examples:

- Pacemaker, either single-chamber or dual-chamber;
- Cardiac Resynchronization Therapy (CRT) including biventricular pacing; and
- Cardioversion and/or Defibrillation.

Some embodiments include methods of treatment of one or more of the above-mentioned treatments in combination with at least one other of the above-mentioned treatments.

In some embodiments, methods for using one or more of the treatment capabilities serially and/or in parallel are provided.

In some embodiments a device packaging together one or more of the following cardiac treatments: Cardiac Contractility Modulation, Cardioversion, Defibrillation, Cardiac Pacing and Cardiac Resynchronization Therapy (CRT) is provided.

An aspect of some embodiments relates to a combined IPG device having several modalities in same device, and enabling selection of modalities based on clinical needs. Example for treatment modality selection can be: Cardiac Contractility Modulation+Implantable Cardioversion/Defibrillation and/or Cardiac Contractility Modulation+CRT and/or Cardiac Contractility Modulation+pacemaker and/or Cardiac Contractility Modulation+Implantable Cardioversion/Defibrillation+CRT and/or Cardiac Contractility Modulation+Implantable Cardioversion/Defibrillation+pacing.

In some embodiments, treatment modality selection is optionally changed after device implantation, potentially enabling optimal treatment for a patient.

In some embodiments, having Implantable Cardioversion/Defibrillation modality together with Cardiac Contractility Modulation potentially enables the following activities:

- stopping Cardiac Contractility Modulation therapy upon detection of arrhythmia that requires defibrillation. In some embodiments, the arrhythmia is automatically sensed by the IPG, which optionally automatically stops providing Cardiac Contractility Modulation. The automatic stopping potentially provides faster reaction than a physician instructing the IPG to stop providing Cardiac Contractility Modulation;
- increasing Cardiac Contractility Modulation dosing for a set time period after a defibrillation event, potentially strengthening the cardiac muscle and helping to prevent additional onset of arrhythmia. In some embodiments the defibrillation event is produced by the IPG, which optionally automatically controls providing Cardiac Contractility Modulation. The automatic control potentially provides Cardiac Contractility Modulation for a defibrillation event even if a physician is not present. In some embodiments, the IPG is optionally pre-programmed to increase Cardiac Contractility Modulation dosing by increasing a number of hours per day in which the Cardiac Contractility Modulation is provided and/or increasing a number of cardiac cycles per day in which the Cardiac Contractility Modulation is provided;
- following defibrillation, suppressing Cardiac Contractility Modulation activity for a set time period, by way of a non-limiting example between 1-90 days or until no arrhythmic event occurs during a specific time period. In some embodiments, the defibrillation is automatically sensed by the IPG, which optionally automatically controls suppressing Cardiac Contractility Modulation. The automatic suppression potentially provides faster reaction than a physician instructing the IPG to stop providing Cardiac Contractility Modulation; and
- using a same lead for Cardiac Contractility Modulation stimulation and optionally also providing defibrillation shock.

In some embodiments, for example when having CRT or pacemaker modalities together with Cardiac Contractility Modulation, the following activities are optionally enabled:

- delivering Cardiac Contractility Modulation treatment during a non-paced heartbeat. In some embodiments, the IPG senses a heartbeat when a pacing signal was not provided, and optionally provides Cardiac Contractility Modulation treatment automatically during such a heartbeat;
- delivering Cardiac Contractility Modulation after a set delay following Right Ventricle (RV) or Left Ventricle (LV) pacing. In some embodiments, the IPG senses when a pacing signal was provided, and optionally provides Cardiac Contractility Modulation treatment automatically, without interfering with the pacing signal;
- using a same electrode for pacing and Cardiac Contractility Modulation. In some embodiments, providing during one cardiac cycle a pacing signal followed by a Cardiac Contractility Modulation signal; and
- using the Cardiac Contractility Modulation signal for both Cardiac Contractility Modulation treatment and pacing.

An aspect of some embodiments includes providing an IPG which includes hardware suitable for providing the cardiac treatments mentioned herein.

In some embodiments, the IPG includes a suitable power supply or power supplies.

In some embodiments, various uses of electric power call for various batteries.

By way of a non-limiting example, in some embodiments, in implantable cardiac devices such as an Implantable Cardioverter Defibrillator (ICD), there are some uses with low current demand (e.g. Cardiac Contractility Modulation therapy, sensing, VT/VF (Ventricular Tachycardia/Ventricular Fibrillation) detection, housekeeping, communications, operation of non-electric-shock components in the implantable device, etc.), and some uses with significantly higher current demand (e.g. cardioversion and/or defibrillation).

In some embodiments, two batteries are included in an implantable device, one battery for low current operations and one battery for high current operations.

In some embodiments, more than two batteries are included.

Some potential advantages of using two batteries included in an implantable device, one battery for low current operations and one battery for high current operations include:

Using a rechargeable battery for low current uses such as Cardiac Contractility Modulation therapy, sensing, VT/VF detection, housekeeping, communications, can potentially keep more electric energy stored in a non-rechargeable battery for uses which draw higher current, such as cardioversion and/or defibrillation.

By way of a non-limiting example, above-mentioned Provisional Patent Application No. 62/957,243 filed Jan. 5, 2020, titled “An Implantable Cardioverter Defibrillator (ICD) device with high longevity”, describes systems with capability for powering differing treatments and methods for managing the systems.

In some embodiments, the IPG includes suitable electrodes and suitable leads for providing electric signals to a heart and/or for sensing physiological parameters.

In some embodiments, the IPG includes suitable electrodes and leads for providing a combination of treatments as described herein.

The table below describes which electrode locations are optionally used for providing which cardiac treatment. The following abbreviations are used in the table: RV=Right Ventricle, RA=Right Atrium, LV=Left Ventricle, VC=Vena Cava.

| Cardiac Treatment | Electrode location |
|---|---|
| Pacing | RA;<br>RV;<br>RA + RV;<br>RA + RV + LV; |
| Cardioversion | Single Coil at RV or RA or VC;<br>2 coils at RV + RA, RV + VC, RA + VC |
| Defibrillation | Single Coil at RV or RA or VC;<br>2 coils at RV + RA, RV + VC, RA + VC |
| Cardiac Resynchronization Therapy (CRT) | RA + RV + LV |
| Cardiac Contractility Modulation | 1-4 RV<br>1-2 LV (optional)<br>RA (optional for sensing) |

In some embodiments, an IPG optionally includes a combination of leads and electrodes which supports two or more of the cardiac treatments described in the table above, that is, the leads are configured to reach the locations of one or more of the electrode positions described above with reference to the cardiac treatments.

In some embodiments, an IPG optionally includes a combination of electrodes which supports two or more of the cardiac treatments described in the table above, that is, the electrodes are located at the locations of one or more of the electrode positions described above with reference to the cardiac treatments.

An aspect of some embodiments relates to activation methods for an IPG with combined Cardiac Contractility Modulation and/or ICD and/or CRT therapy.

In some embodiments, a method is described for increasing Cardiac Contractility Modulation dosing for a set time period after a defibrillation event. Such stimulation may potentially strengthen the cardiac muscle and help prevent additional onset of Arrhythmia.

In some embodiments, following a defibrillation event, a method is provided which optionally suppresses Cardiac Contractility Modulation activity for a set time period (between 1-90 days) and/or until an arrhythmia level is below a set threshold (for example 1 arrhythmia event per 1 min).

In some embodiments, a method is provided which, following provision of an anti-tachycardia pacing mode, provides pacing using a “Cardiac Contractility Modulation”-like pulse pattern, such as, by way of a non-limiting example, a biphasic pulse with a pulse width of, for example, 10 mS. In some instances, such a method potentially provides a better anti-tachycardia effect, by breaking a reentry cycle in the heart.

An aspect of some embodiments relates to activation methods for an IPG with combined Cardiac Contractility Modulation, CRT and ICD.

In some embodiments, for example for patients with a varied Heart Failure (HF) condition (for example deterioration), a selection of modalities is optionally evaluated by a physician, optionally based on patient needs, and optionally input to an IPG device as a program for activation a sequence of treatment modalities.

In some embodiments, a selection method is optionally based on machine learning and/or personalization of activation parameters.

In some embodiments, the selection method is optionally based on machine learning of activation parameters and/or treatment modality sequences based on a population of patients. In some embodiments the patients are grouped into similarity groups, for providing the machine learning modules, by a physician, optionally based on the patients’ condition and/or based on the patients having similar IPG devices.

In some embodiments, an evaluation process is optionally based on information from sensors that are part of or connected to the IPG or from external units that evaluate the patient condition. In some embodiments, a treatment method or combination is optionally selected based, at least in part, on the evaluation. Some non-limiting examples of sensors include: implanted and/or external sensors for blood pressure, ECG, breathing rate. In some embodiments, the evaluation optionally includes analyzing an ECG signal (optionally at various frequencies), and detecting arrhythmia. In some embodiments, the evaluation optionally includes analyzing bio-impedance for measurement of potential congestion.

In some embodiments, an evaluation process is optionally based on one or more considerations such as blood tests, cardiac imaging and biopsy.

Figure 1B:
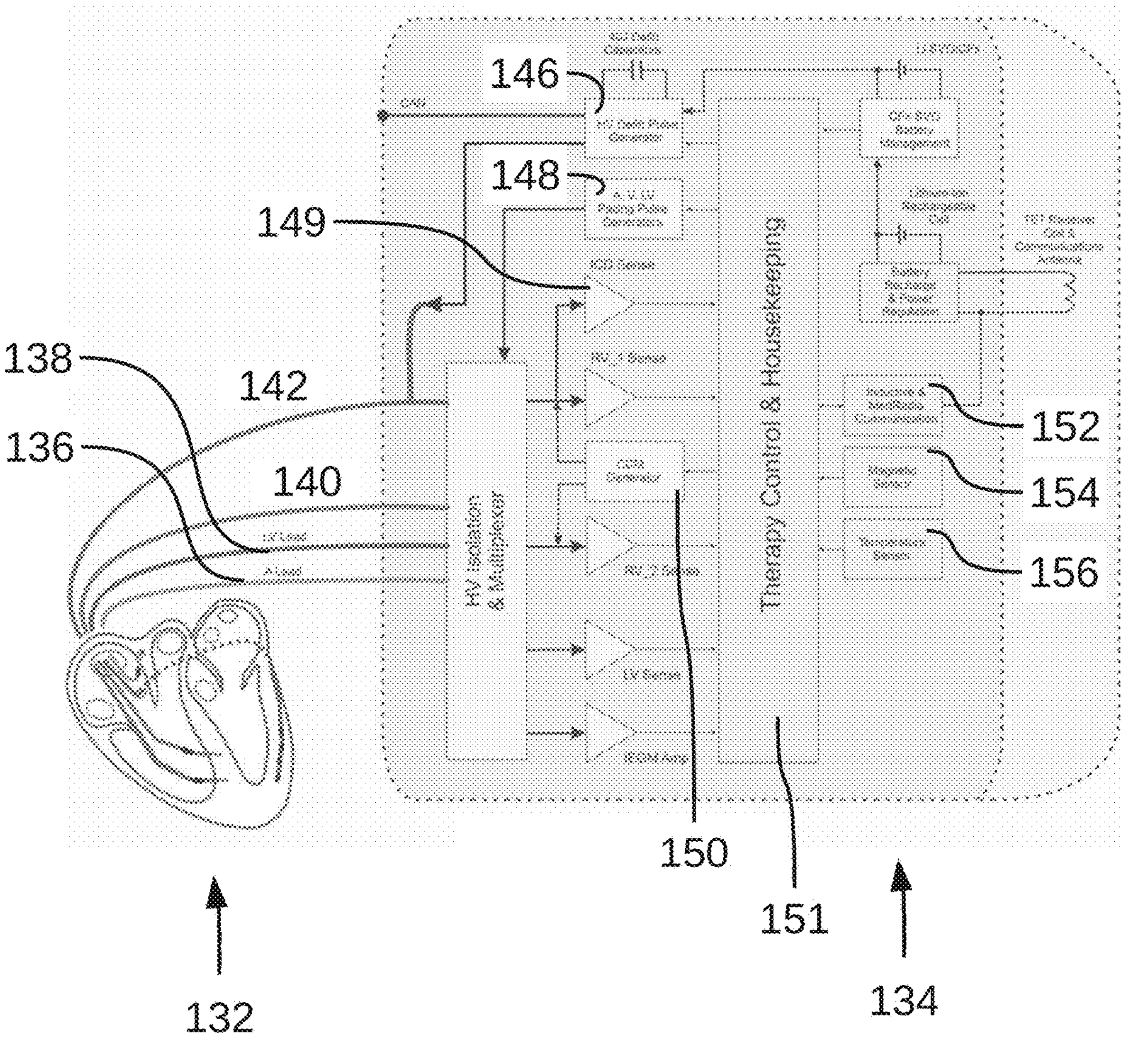
FIG. 1B is a simplified illustration showing an IPG and leads placed in a heart.

In some embodiments, a physician performs the evaluation and provides a treatment program to the IPG device, optionally to a therapy control and housekeeping module such as displayed in FIG. 1B.

In some embodiments, a therapy control module within the IPG, such as, for example, the therapy control module 151 displayed in FIG. 1B, receives input from sensors and optionally performs the evaluation and/or a determination of a treatment program, optionally automatically determining the treatment program.

Some non-limiting examples of potential cardiac treatment activation sequences include:

- performing defibrillation by rapid pacing, optionally followed by cardioversion shock;
- performing defibrillation, optionally followed by Cardiac Contractility Modulation;
- performing defibrillation, and if heart rhythm is improved, optionally follow by providing Cardiac Contractility Modulation;
- performing cardioversion using rapid cardiac pacing; and
- performing Cardiac Resynchronization Therapy followed by Cardiac Contractility Modulation.

In some embodiments, improvement of heart condition is optionally determined based on one or more of clinical procedures such as measuring ejection fraction, and/or classification of a patient's state according to New York Heart Association (NYHA) Classification, and/or results of a six minute walk test.

An aspect of some embodiments relates to activation methods for an IPG with a combined Cardiac Contractility Modulation/CRT configuration:

In some embodiments Cardiac Contractility Modulation treatment is optionally delivered during cardiac cycles that do not include CRT pacing. In some embodiments, Cardiac Contractility Modulation treatment is optionally delivered based on a duration of atrioventricular (AV) delay and/or a heart rate of a patient. In some embodiments the Cardiac Contractility Modulation treatment is optionally provided only during cardiac cycles that do not include CRT pacing. In some embodiments, the Cardiac Contractility Modulation treatment is optionally provided during a specific percentage of such cardiac cycles. In some embodiments, the Cardiac Contractility Modulation treatment is optionally provided during such cardiac cycles, however not only during such cardiac cycles.

In some embodiments, following delivery of CRT pacing, a Cardiac Contractility Modulation pulse is optionally provided in reverse polarity.

An aspect of some embodiments relates to pacing methods for an IPG with combined Cardiac Contractility Modulation and/or pacemaker capabilities.

In some embodiments, following delivery of defibrillation therapy, Cardiac Contractility Modulation therapy is optionally provided.

In some embodiments, the pacing methods are specifically applied for treatment of sick sinus syndrome. In some embodiments, a physician decides in what case to apply the pacing methods for sick sinus syndrome, based on the physician's determination that the patient has sick sinus syndrome.

In some embodiments, Cardiac Contractility Modulation treatment is optionally provided only during a cardiac cycle triggered by the pacemaker.

In some embodiments, Cardiac Contractility Modulation treatment is optionally delivered during non-paced cardiac cycles.

In some embodiments, the Cardiac Contractility Modulation treatment is optionally delivered during cardiac cycles associated with a Heart Rate (HR) within a specific range, by way of a non-limiting example a range between 60-80 Beats Per Minute (BPM).

Reference is now made to the construction and operation of an IPG according to an example embodiment of the invention.

FIG. 1A is a simplified illustration showing an IPG and leads placed in a heart.

FIG. 1A shows an IPG 104, with leads 108 110 112 114 placed in a heart 102. A first lead 108 is placed in the right atrium of the heart; a second lead 110 is placed in the left ventricle of the heart; a third lead 112 is placed in a first location in the right ventricle of the heart; and a fourth lead 114 is placed in a second location in the right ventricle of the heart.

FIG. 1A also shows a location of a shock coil 116 included in the third lead 112, and an envelope 106, termed the can 106 of the IPG 104.

By way of a non-limiting example, FIG. 1A shows where the left bottom lead 112 optionally has both a coil and optionally 2 electrodes (termed a bi-polar configuration) that can optionally be used both for sensing and pacing.

In some embodiments, electrodes on leads, such as, by way of a non-limiting example, the above-mentioned leads 108 110 112 114 in the heart, are optionally used for electrical sensing and stimulation/pacing.

In some embodiments, electrodes on leads, such as, by way of a non-limiting example, the above-mentioned leads 108 110 112 114 in the heart, are optionally used for stimulation and/or pacing.

In some embodiments, electrodes on leads, such as, by way of a non-limiting example, the above-mentioned leads 108 110 112 114 in the heart, are optionally used for both electrical sensing and/or stimulation and/or pacing.

In some embodiments, electrodes or sensors are optionally added to an IPG, and are optionally located in and/or outside of a heart, optionally for sensing bio-impedance and/or blood pressures.

In some embodiments, a shock coil, such as, by way of a non-limiting example, the above-mentioned shock coil 116 on the, by way of a non-limiting example, third lead 112, is optionally used for defibrillation treatment.

In some embodiments, a lead, such as, by way of a non-limiting example, the above-mentioned lead 110 in the left ventricle of the heart, is optionally used for Cardiac Resynchronization Therapy.

In some embodiments, leads, such as, by way of a non-limiting example, the above-mentioned lead 108 in the right atrium and one or more of the leads 112 114 in the left ventricle, are optionally used for providing pacing treatment.

In some embodiments, leads, such as, by way of a non-limiting example, one or more of the above-mentioned leads 112 114 in the left ventricle, are optionally used for providing Cardiac Contractility Modulation treatment.

Reference is now made to FIG. 1B, which is a simplified illustration showing an IPG and leads placed in a heart.

FIG. 1B is intended to show more details of components of an IPG.

FIG. 1B shows an IPG 134, with leads 136 138 140 142 placed in a heart 132. A first lead 138 is placed in the right atrium of the heart; a second lead 138 is placed in the left ventricle of the heart; a third lead 142, V1/ICD lead, is placed in a first location in the right ventricle of the heart; and a fourth lead 140 is placed in a second location in the right ventricle of the heart.

FIG. 1B also shows a therapy control module 151, a HV Defibrillator Pulse Generator 146, a Pacing Pulse Generator 148, an ICD sensor 149; a Cardiac Contractility Modulation Generator 150; a communication module 152; an optional magnetic sensor 154; and an optional temperature sensor 156.

In some embodiments, cardioversion and/or defibrillation therapy is optionally provided to: one or more electrodes in the right ventricle, and/or one or more leads in the left ventricle In some embodiments, Cardiac Contractility Modulation therapy is optionally provided to one or more electrodes in the right ventricle.

In some embodiments, Cardiac Contractility Modulation is optionally provided to one or more electrodes in the left ventricle, in addition to electrodes in the right ventricle.

In some embodiments, Cardiac Contractility Modulation is optionally provided using an electrodes in the right atrium, used for sensing.

Figure 2:
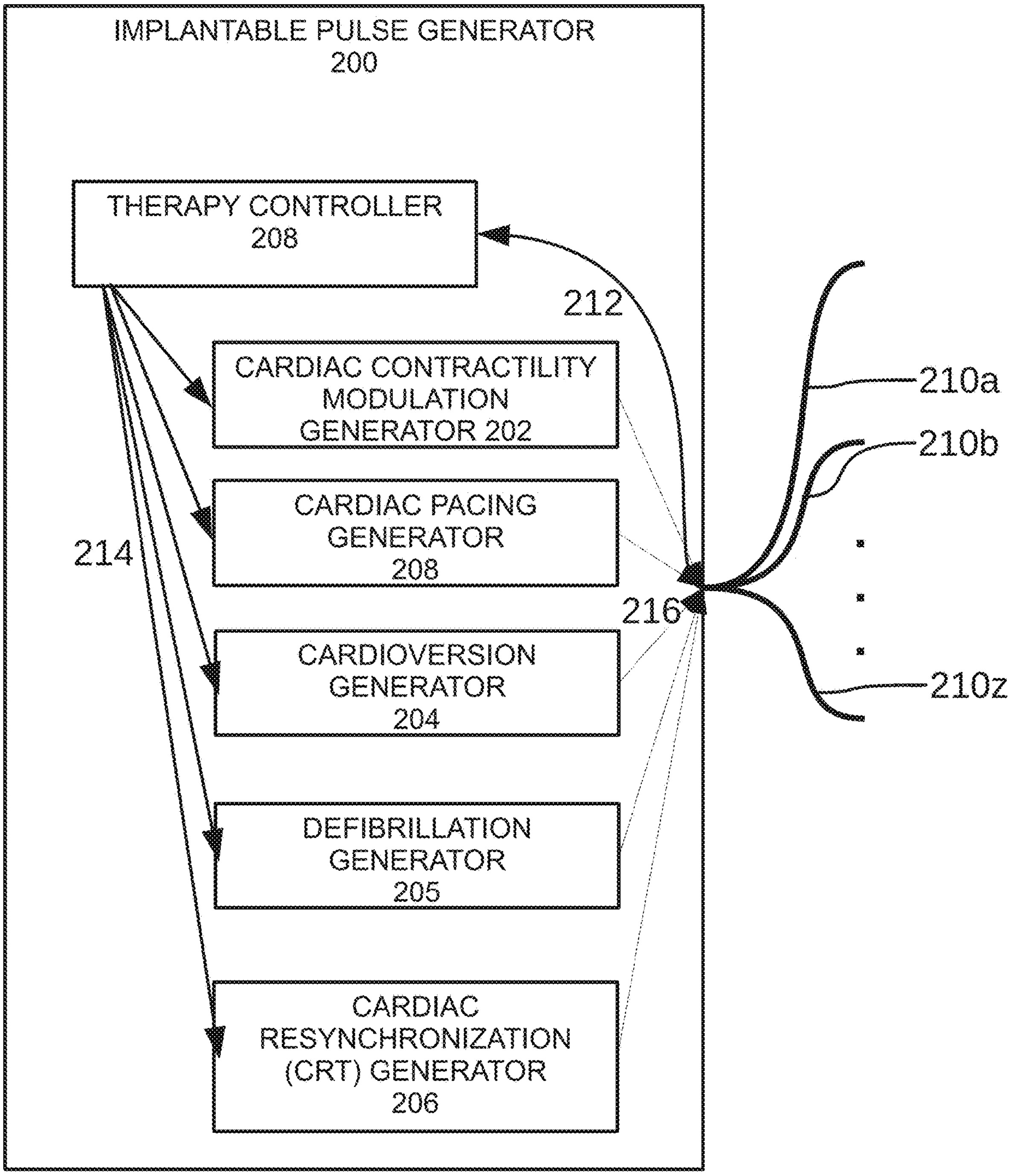
FIG. 2 is a simplified block diagram illustration of an IPG and leads according to an example embodiment.

Reference is now made to FIG. 2, which is a simplified block diagram illustration of an IPG and leads according to an example embodiment.

FIG. 2 shows an IPG 200, and a plurality of leads 210*a* 210*b* . . . 210*z*. In various example embodiments the number of leads may be different—by way of some non-limiting examples 2, 3, 4, 5, 6, 7, 8 leads, and so on, up to, for example more than 8 leads.

In some embodiments, leads are optionally used for multiple treatment modalities. In some embodiments, a same lead is used both for defibrillation and for pacing and/or Cardiac Contractility Modulation.

In some embodiments, one or more of the leads 210 210*b* . . . 210*z* can optionally be used both for sensing and for providing a cardiac treatment modality.

In some embodiments, the leads 210 provide one or more 212 sensing signal(s) to a therapy controller 208, which determines which therapy, if any, is to be provided via lead(s) 210 to the heart.

In some embodiments, the therapy controller 208 optionally determines which therapy is to be administered, if any, and controls 214 one or more pulse generators 202 204 205 206 208 to provided 216 pulses via the leads 210 to a patient.

In the example embodiment shown in FIG. 2, the IPG 200 includes modules for providing Cardiac Contractility Modulation therapy 202, cardioversion 204 and/or defibrillation 205 and cardiac resynchronization 206.

In some embodiments, the IPG 200 includes less modules than the number of therapy types, for example one or two modules (not shown in FIG. 2) for providing one or more of Cardiac Contractility Modulation therapy, cardioversion/defibrillation and cardiac resynchronization.

In some embodiments, the IPG 200 includes modules which combine two or more therapy types, for example combine generating signals for cardioversion and defibrillation.

Figure 3A:
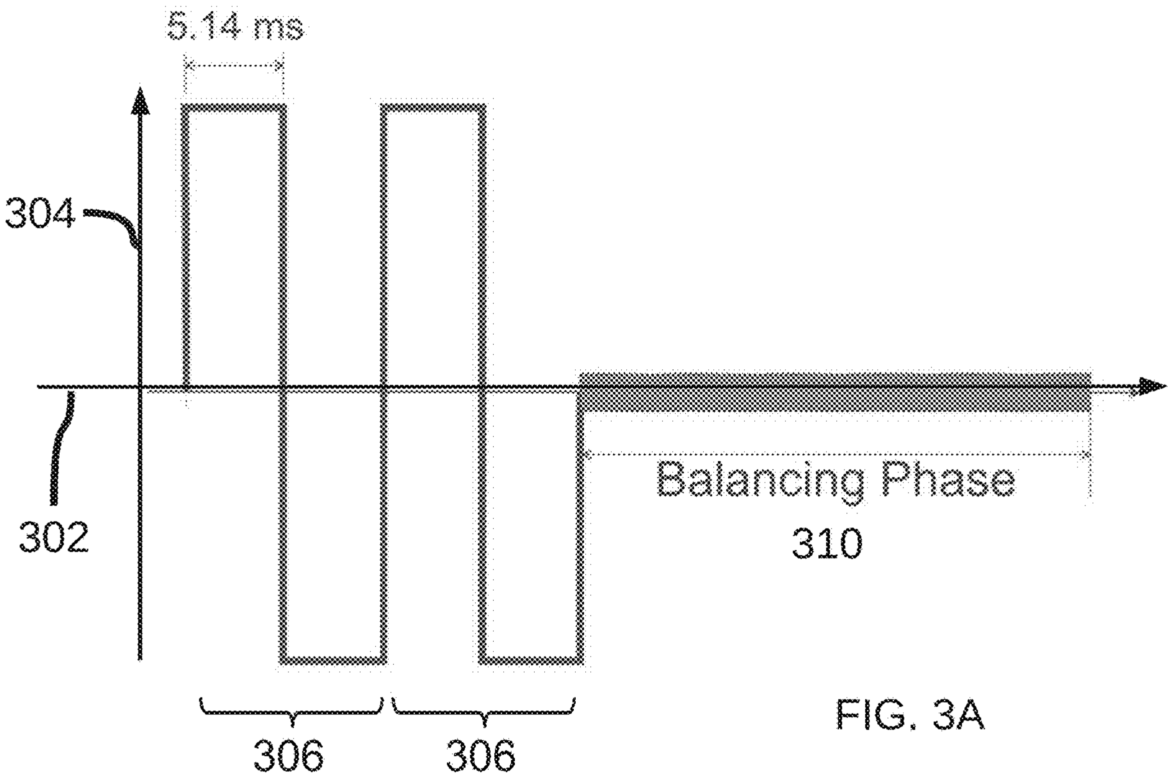
FIG. 3A is a simplified illustration of a graph of Cardiac Contractility Modulation stimulation, according to an example embodiment.

Reference is now made to FIG. 3A, which is a simplified illustration of a graph of Cardiac Contractility Modulation stimulation, according to an example embodiment.

FIG. 3A shows a graph with an X-axis 302 of time, and a Y-axis 304 of voltage applied at Cardiac Contractility Modulation leads. FIG. 3A shows a non-limiting example of a Cardiac Contractility Modulation pulse pattern. FIG. 3A shows a series of two biphasic pulses 306, each pulse with an example typical width of 5.14 milliseconds. The pulses are followed by a balancing phase 310 or balancing period 310.

Figure 3B:
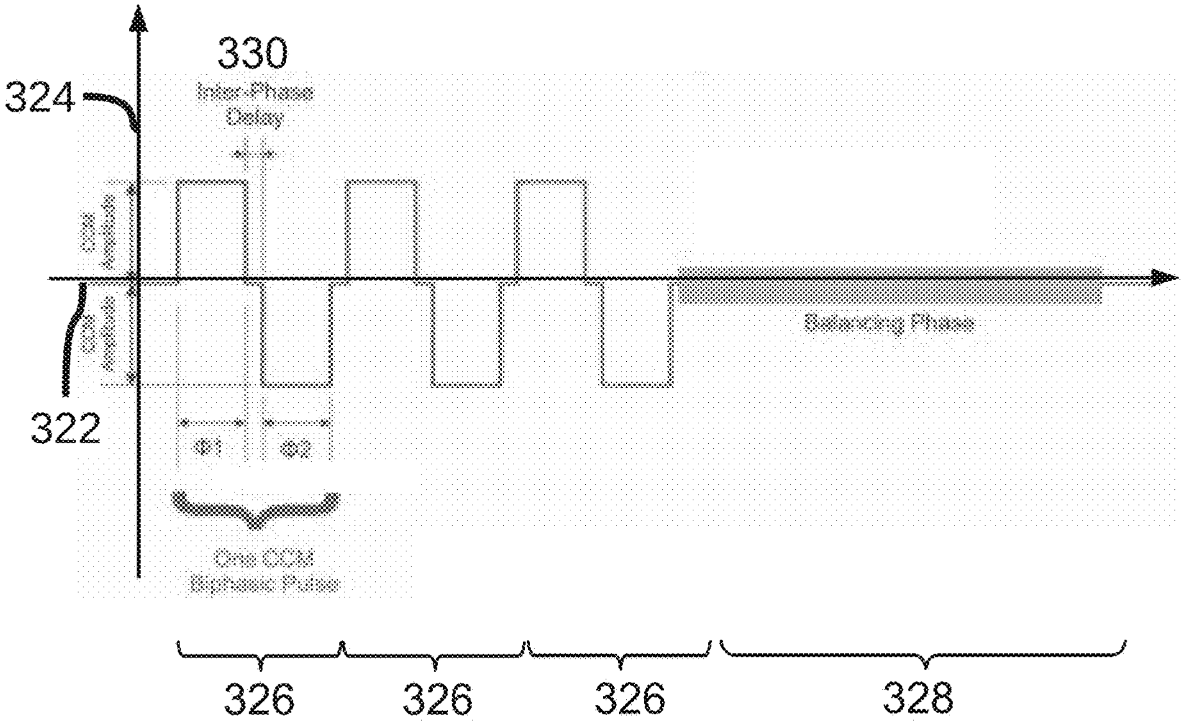
FIG. 3B is a simplified illustration of a graph of Cardiac Contractility Modulation stimulation, according to an example embodiment.

Reference is now made to FIG. 3B, which is a simplified illustration of a graph of Cardiac Contractility Modulation stimulation, according to an example embodiment.

FIG. 3B shows a graph of Cardiac Contractility Modulation stimulation over 1 lead, either one of Channel 1 or Channel2, or Cardiac Contractility Modulation stimulation over 2 leads in parallel, both Channel 1 and Channel2, synchronized to provide Cardiac Contractility Modulation stimulation simultaneously along both channels. In some embodiments, when Cardiac Contractility Modulation stimulation is provided via two channels, there is a delay between start of the stimulation in one channel relative to the other channel.

FIG. 3B shows a non-limiting example of a Cardiac Contractility Modulation pulse pattern. FIG. 3B shows a graph with an X-axis 322 of time, and a Y-axis 324 of voltage applied at Cardiac Contractility Modulation leads. FIG. 3B shows a series of three biphasic pulses 326, each pulse with an example typical width of 5.14 milliseconds. The pulses are followed by a balancing phase 328 or balancing period 328.

FIG. 3B shows biphasic pulses 326 where the pulses are optionally provided with an inter-phase delay 330 between a positive phase and a negative phase, and in some embodiments a same or differently sized inter-phase delay between pairs of positive and negative pulses, that is, between the bi-phasic pulses 326.

Figure 3C:
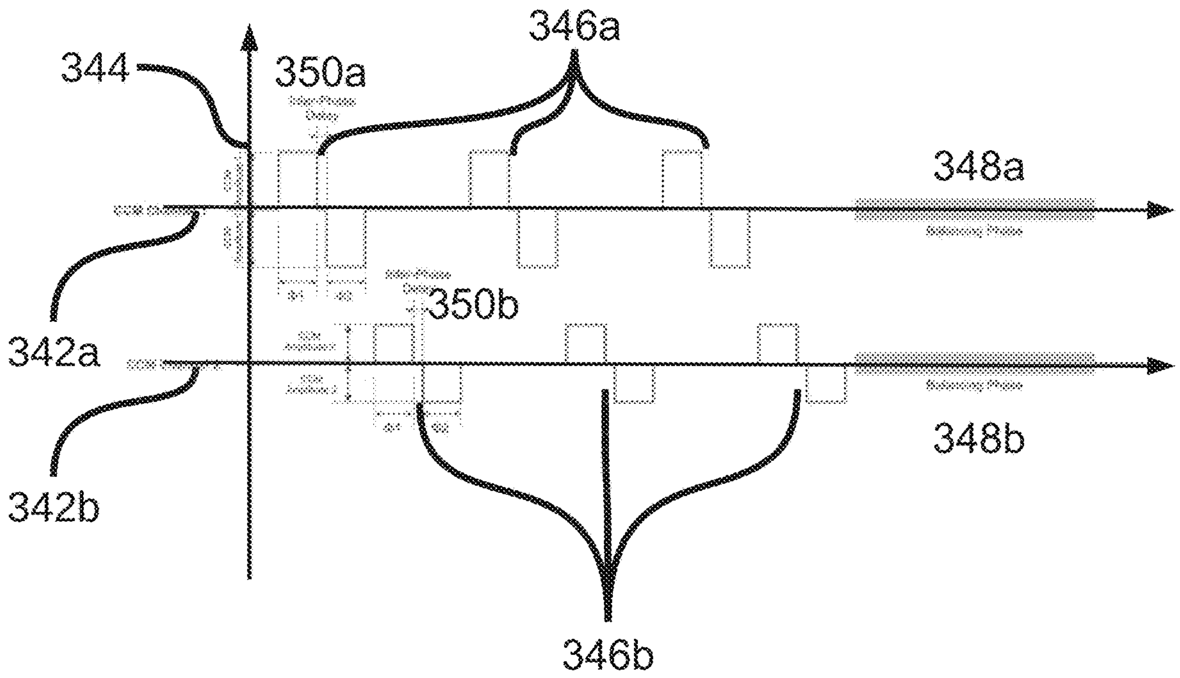
FIG. 3C is a simplified illustration of a graph of Cardiac Contractility Modulation stimulation over 2 leads, according to an example embodiment.

Reference is now made to FIG. 3C, which is a simplified illustration of a graph of Cardiac Contractility Modulation stimulation over 2 leads, according to an example embodiment.

FIG. 3C shows a graph of Cardiac Contractility Modulation stimulation over 2 leads, also named Channel 1 and Channel2. FIG. 3C shows a graph of Cardiac Contractility Modulation stimulation pulses where the pulses are interleaved in time, one by one.

FIG. 3C shows a non-limiting example of a Cardiac Contractility Modulation pulse pattern. FIG. 3C shows a graph with two X-axes 342*a* 342*b* of time, and a Y-axis 344 of voltage applied at the Cardiac Contractility Modulation leads. The two X-axes 342*a* 342*b* show a time for each one of Channel 1 and Channel 2 respectively. The two X-axes 342*a* 342*b* are aligned to each other. The Y axis 344 of voltage shows voltage such that the zero voltage of Channel 1 is at the height of the intersection of the Channel 1 X-axis 342*a* and the Y-axis 344, and the zero voltage of Channel 2 is at the height of the intersection of the Channel 2 X-axis 342*b* and the Y-axis 344.

FIG. 3C shows a series of three biphasic pulses 346*a* as applied to Channel 1, and three biphasic pulses 346*b* as applied to Channel 2. In the example of FIG. 3C, each bi-phasic pulse has a positive portion with a width of $\Phi_1$, and a negative portion with a width of $\Phi_2$.

In some embodiments, an absolute value of the amplitude of the positive portion is optionally equal to an absolute value of the amplitude of the negative portion. In some embodiments, an absolute value of the amplitude of the positive portion is optionally not equal to an absolute value of the amplitude of the negative portion.

In some embodiments, a duration of the positive portion is optionally equal to a duration of the negative portion. In some embodiments, the duration of the positive portion is optionally not equal to the duration of the negative portion.

In some embodiments, a total electric charge provided by the positive portion of one pulse is optionally equal to a total electric charge provided by the negative portion of the one pulse.

In some embodiments, a total electric charge provided by the positive portions of a number of pulses provided during a pulse train is optionally equal to a total electric charge provided by the negative portion of the number of pulses provided during a pulse train.

In some embodiments, each channel optionally has a balanced stimulation, and the amplitude of the stimulation is equal in both channels.

In some embodiments, each channel optionally has a balanced stimulation, and the amplitude of the stimulation is not equal in both channels.

In some embodiments, the amplitude of the stimulation is optionally determined based on location of the electrodes in a heart, the electrode's impedance, and the heart's bio-impedance.

FIG. 3C shows biphasic pulses 346*a* 346*b* where the pulses are optionally provided with inter-phase delays 350*a* 350*b* between a positive phase and a negative phase, and in some embodiments a same or differently sized inter-phase delay between pairs of positive and negative pulses, that is, between the bi-phasic pulses 346*a* 346*b*.

Figure 3D:
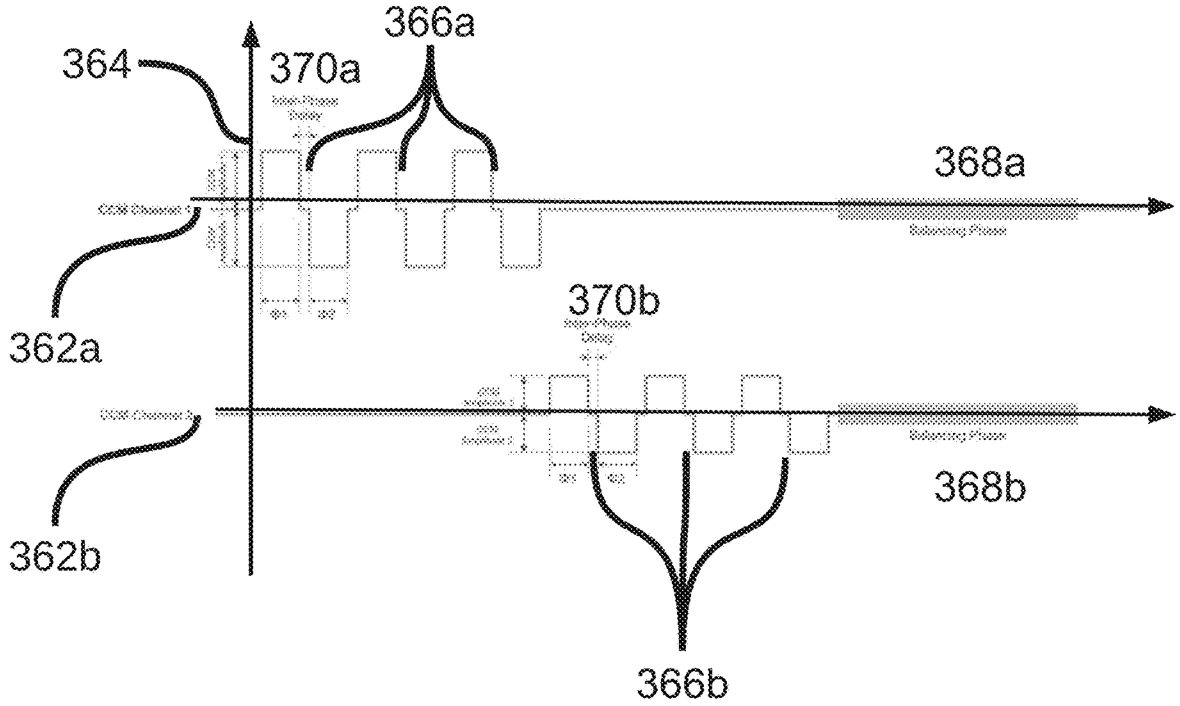
FIG. 3D is a simplified illustration of a graph of Cardiac Contractility Modulation stimulation over 2 leads, according to an example embodiment.

Reference is now made to FIG. 3D, which is a simplified illustration of a graph of Cardiac Contractility Modulation stimulation over 2 leads, according to an example embodiment.

FIG. 3D shows a graph of Cardiac Contractility Modulation stimulation over 2 leads, also named Channel 1 and Channel2. FIG. 3D shows a graph of Cardiac Contractility Modulation stimulation pulses where a train of $n_1$ pulses on one channel, for example Channel 1, is followed by a train of $n_2$ pulses on the other channel, for example Channel 2. FIG. 3D shows a case where $n_1=n_2=3$, however the number of pulses is not necessarily 3, and the number of pulses is not necessarily equal over different channels.

FIG. 3D shows a non-limiting example of a Cardiac Contractility Modulation pulse pattern. FIG. 3D shows a graph with two X-axes 362*a* 364*b* of time, and a Y-axis 364 of voltage applied at the Cardiac Contractility Modulation leads. The two X-axes 362*a* 362*b* show a time for each one of Channel 1 and Channel 2 respectively. The two X-axes 362*a* 362*b* are aligned to each other. The Y axis 364 of voltage shows voltage such that the zero voltage of Channel 1 is at the height of the intersection of the Channel 1 X-axis 362*a* and the Y-axis 364, and the zero voltage of Channel 2 is at the height of the intersection of the Channel 2 X-axis 362*b* and the Y-axis 364.

FIG. 3D shows a series of three biphasic pulses 366*a* as applied to Channel 1, and three biphasic pulses 366*b* as applied to Channel 2. In the example of FIG. 3D, each bi-phasic pulse has a positive portion with a width of $\Phi_1$, and a negative portion with a width of $\Phi_2$.

It is noted that typically a positive amplitude and a negative amplitude of a bi-phasic pulse are optionally equal.

In some embodiments, a positive amplitude and a negative amplitude of a bi-phasic pulse can optionally be not equal.

FIG. 3D shows the pulses followed by balancing phases 368*a* 368*b*, or balancing periods 368*a* 368*b* for Channel 1 and Channel 2 respectively.

FIG. 3D shows biphasic pulses 366*a* 366*b* where the pulses are optionally provided with inter-phase delays 370*a* 370*b* between a positive phase and a negative phase, and in some embodiments a same or differently sized inter-phase delay between pairs of positive and negative pulses, that is, between the bi-phasic pulses 366*a* 366*b*.

Figure 4A:
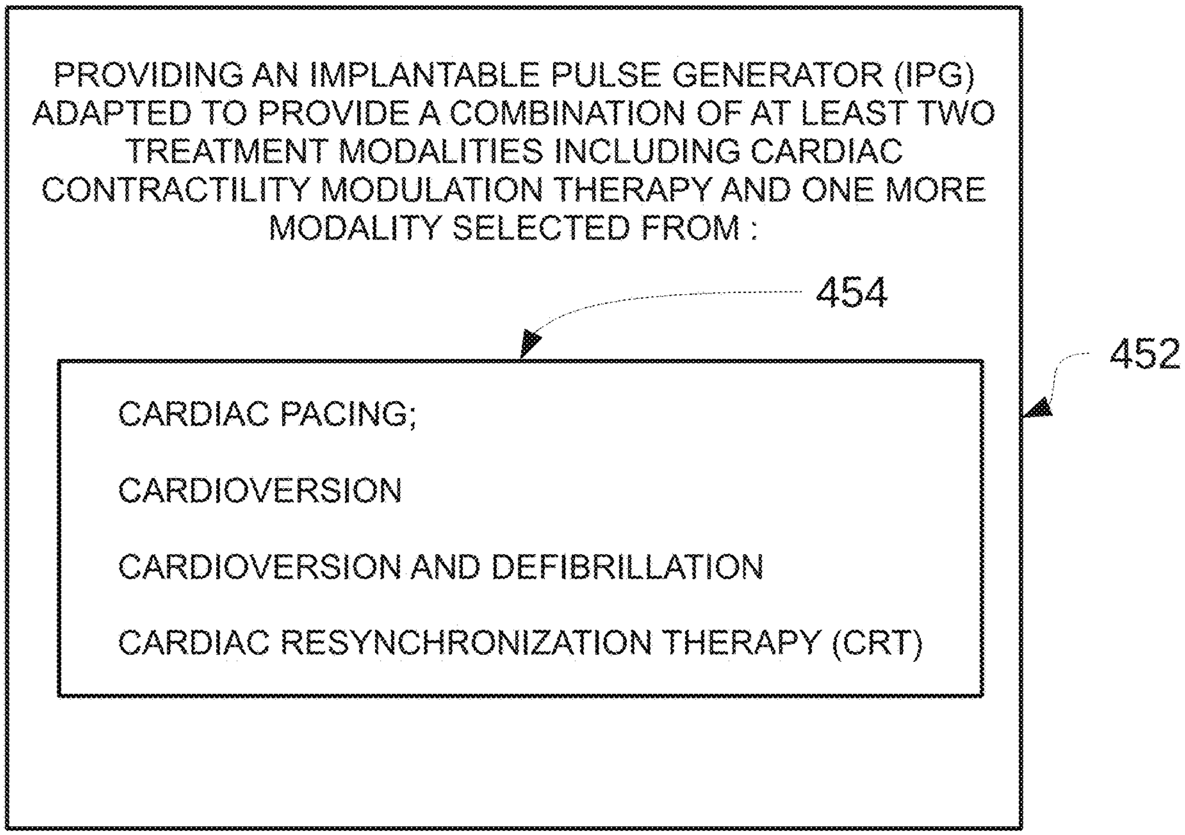
FIG. 4A is a simplified flow chart diagram of a method of treating a heart according to an example embodiment.

Reference is now made to FIG. 4A, which is a simplified flow chart diagram of a method of treating a heart according to an example embodiment.

The method of FIG. 4A includes:

providing an Implantable Pulse Generator (IPG) adapted to provide a combination of at least two treatment modalities (452) including Cardiac Contractility Modulation Therapy and one more modality selected from a group consisting of:

Cardiac pacing;

Cardioversion and/or Defibrillation; and

Cardiac Resynchronization Therapy (CRT) (454).

In some embodiments, the treatment modalities are provided together within a duration of one heartbeat.

In some embodiments, the treatment modalities are provided in sequence within a duration of one heartbeat, when one treatment modality ends, another treatment modality is provided.

Figure 4B:
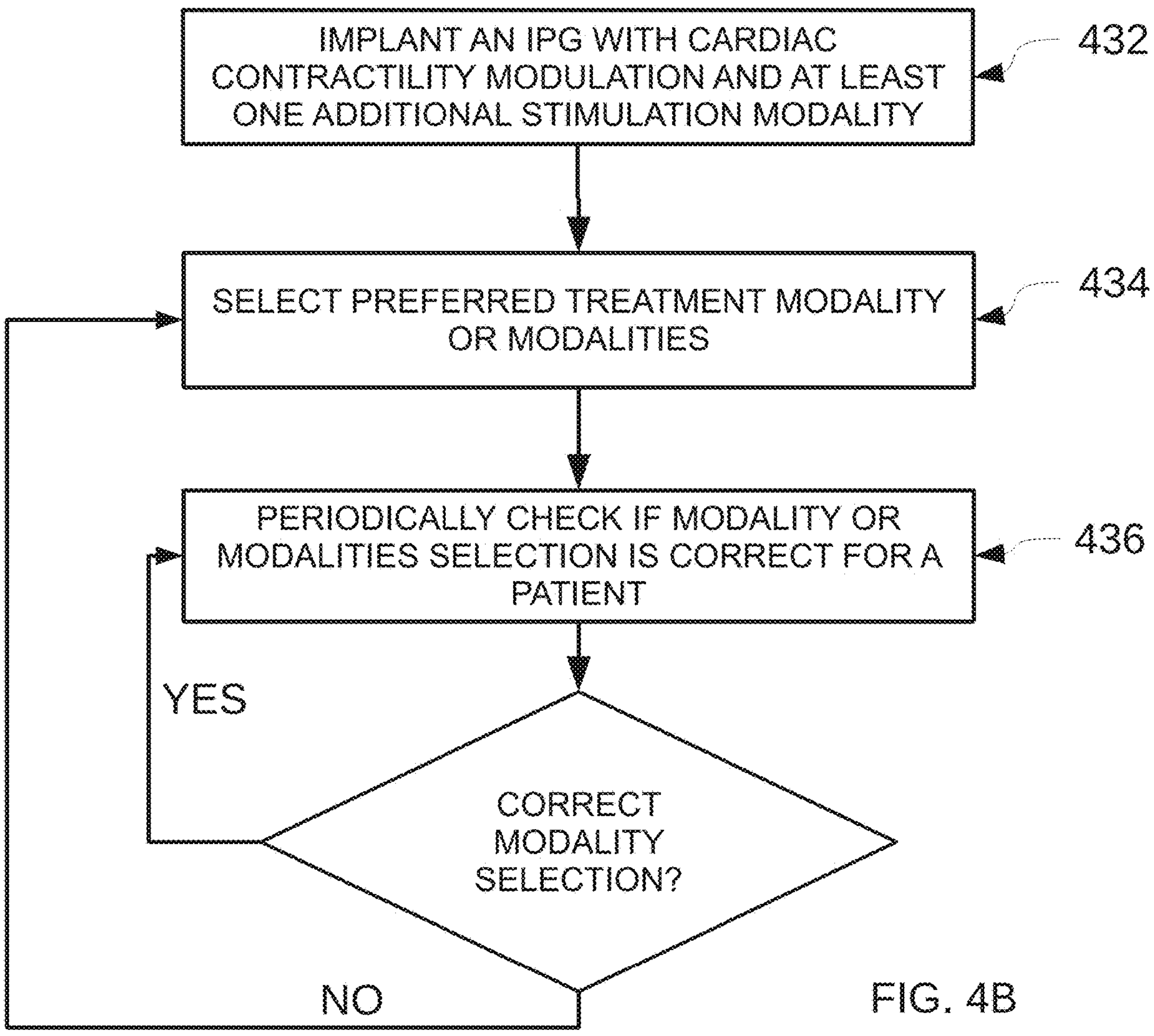
FIG. 4B is a simplified flow chart diagram of a method of treating a heart using an implantable pulse generator according to an example embodiment.

Reference is now made to FIG. 4B, which is a simplified flow chart diagram of a method of treating a heart using an implantable pulse generator according to an example embodiment.

FIG. 4B shows a method of implanting an Implantable Pulse Generator (IPG) and selecting a preferred treatment modality.

The method of FIG. 4B includes:

Implanting an IPG with Cardiac Contractility Modulation and at least one additional stimulation modality (432);

selecting a preferred treatment modality or modalities (434);

periodically checking if modality or modalities selection is correct for a patient (436);

if the modality or modalities selection is correct, then continue periodically checking (436);

else return to selecting a preferred treatment modality or modalities (434).

In some embodiments, the selecting a preferred treatment modality is optionally performed by a control module such as, by way of a non-limiting example, the therapy control module 151 shown in FIG. 1B. In some embodiments, the control module automatically selects a preferred treatment, optionally based on receiving data from sensors, and/or receiving an external signal.

Figure 4C:
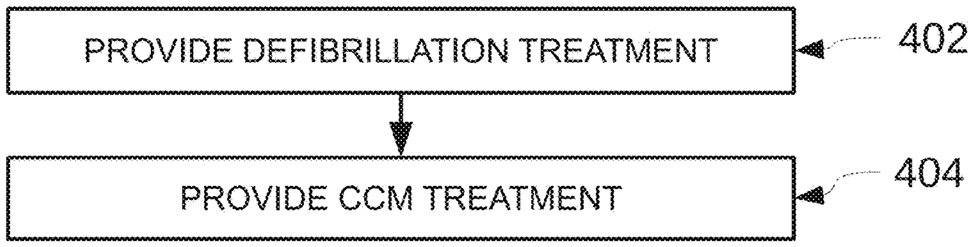
FIG. 4C is a simplified flow chart diagram of a method of treating a heart using an implantable pulse generator according to an example embodiment.

Reference is now made to FIG. 4C, which is a simplified flow chart diagram of a method of treating a heart using an implantable pulse generator according to an example embodiment.

FIG. 4C shows a method of providing Cardiac Contractility Modulation treatment after providing defibrillation treatment.

The method of FIG. 4C includes:

providing defibrillation treatment (402); and following the providing the defibrillation treatment, providing Cardiac Contractility Modulation treatment (404).

In some embodiments, the providing the Cardiac Contractility Modulation treatment optionally performed by a control module such as, by way of a non-limiting example, the therapy control module 151 shown in FIG. 1B. In some embodiments, the control module automatically selects a preferred treatment, optionally based on receiving data from sensors, and/or receiving an external signal.

It is noted that providing Cardiac Contractility Modulation treatment after providing de-fibrillation treatment potentially strengthens the cardiac muscle, and/or potentially prevents or reduces likelihood of onset of arrhythmia.

In some embodiments, Cardiac Contractility Modulation treatment is provided a set time after defibrillation treatment.

In some embodiments, Cardiac Contractility Modulation treatment is provided after defibrillation treatment, a set time after fibrillation is no longer detected.

In some embodiments, Cardiac Contractility Modulation treatment is provided after defibrillation treatment, when an arrhythmia level falls below a specific threshold.

By way of some non-limiting examples, the threshold is when a patient has less than 5%, 10%, 15% and 20% premature ventricular contractions (PVCs).

In some embodiments, Cardiac Contractility Modulation treatment is provided unless a patient has an increase in rate of PVCs greater than 0%, 10%, 20%, 50%, 100% relative to the patient's previous history of rate of PVCs.

Figure 4D:
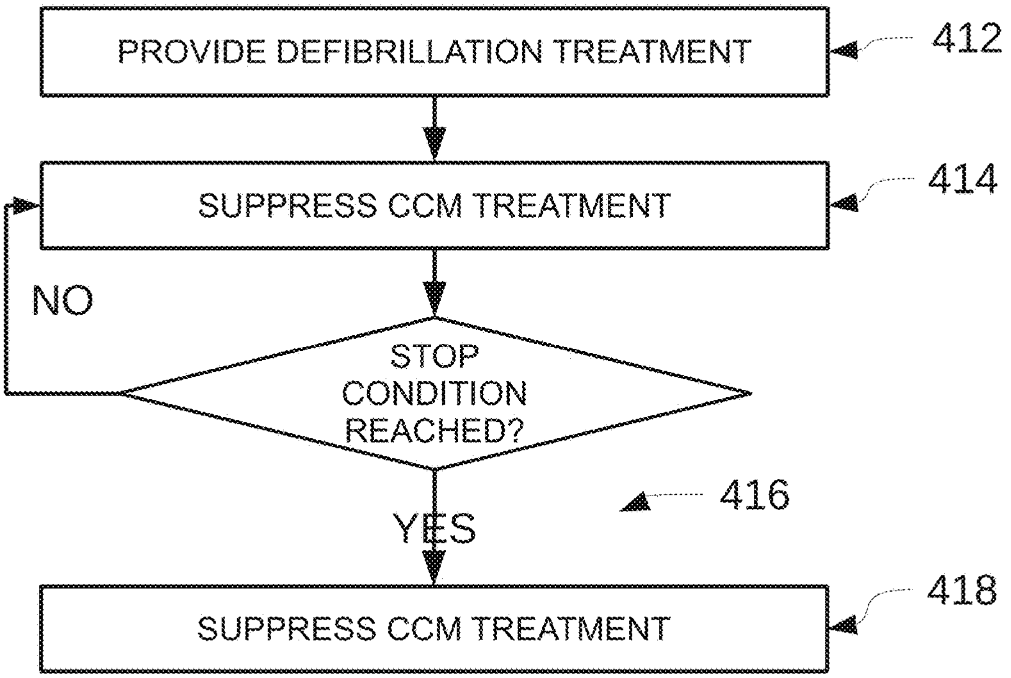
FIG. 4D is a simplified flow chart diagram of a method of treating a heart using an implantable pulse generator according to an example embodiment.

Reference is now made to FIG. 4D, which is a simplified flow chart diagram of a method of treating a heart using an implantable pulse generator according to an example embodiment.

FIG. 4D shows a method of providing Cardiac Contractility Modulation treatment after providing defibrillation treatment.

The method of FIG. 4D includes:

providing defibrillation treatment (412);

following the providing the defibrillation treatment, suppressing providing Cardiac Contractility Modulation treatment (414);

check if a stop condition for the suppressing has been reached (416); and if the stop condition has been reached, then start providing Cardiac Contractility Modulation treatment (418);

else continue suppressing providing Cardiac Contractility Modulation treatment (414).

In some embodiments, the checking if a stop condition for the suppressing has been reached is performed by a control module such as, by way of a non-limiting example, the therapy control module 151 shown in FIG. 1B.

An aspect of some embodiments includes, in the event of providing anti-tachycardia pacing treatment, provide the pacing using a "Cardiac Contractility Modulation" like pulse pattern, such as shown in FIGS. 3A, 3B, 3C and 3D. For example providing a biphasic pulse with pulse width of 10 mS. In some embodiments, a width of a bi-phasic pulse is optionally in a range between, by way of some non-limiting examples, 1-20 mS, 5-20 mS, 8-12 mS, or 9-11 mS. In some embodiments such treatment potentially generates a better anti-tachycardia effect than previously, potentially by breaking the reentry cycle in the heart.

Figure 5:
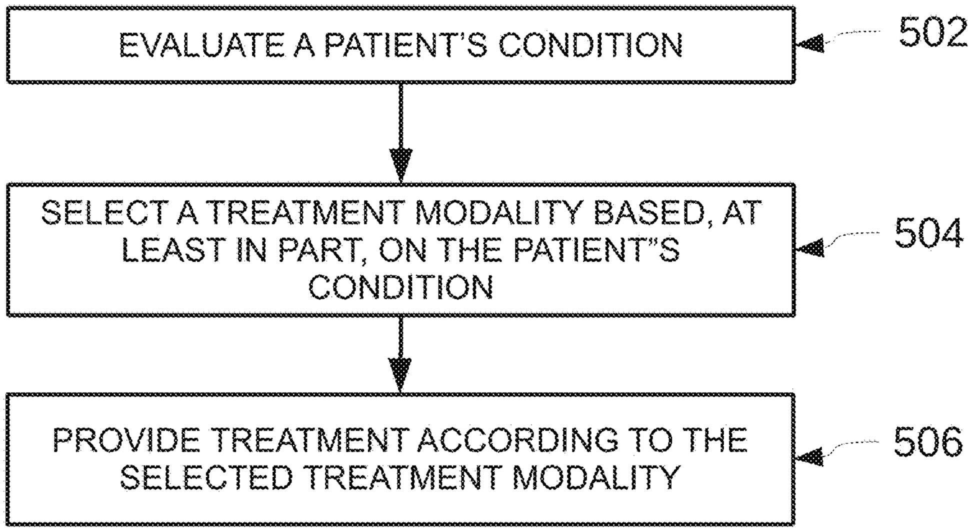
FIG. 5 is a simplified flow chart diagram of a method of treating a heart using an implantable pulse generator (IPG) according to an example embodiment.

Reference is now made to FIG. 5, which is a simplified flow chart diagram of a method of treating a heart using an implantable pulse generator (IPG) according to an example embodiment.

FIG. 5 shows a method of selecting a treatment modality based on evaluating a patient's condition.

The method of FIG. 5 includes:

evaluating a patient's condition (502);

selecting a treatment modality (504); and providing treatment according to the selected treatment modality (506).

In some embodiments, evaluating the patient's condition includes determining the patient's condition based on analyzing electrical signals obtained by the sensors that are part of or connected to the IPG.

In some embodiments, evaluating the patient's condition includes determining the patient's condition based on analyzing electrical signals obtained from sensors that are from external units that evaluate the patient condition.

In some embodiments the analysis includes analyzing one or more of: ECG signals, whether from implanted sensors or external sensors; blood pressure; bio-impedance; and arrhythmia.

In some embodiments, evaluating the patient's condition includes detecting a deterioration in the patient's condition.

By way of some non-limiting examples, detecting a deterioration in the patient's condition optionally includes a physician detecting one or more of sick sinus syndrome and/or heart failure which, according to medical guidelines, indicates need for Cardioversion and/or Defibrillation and/or Cardiac Resynchronization Therapy and/or Cardiac Contractility Modulation.

In some embodiments, evaluating the patient's condition includes using machine learning to evaluate the electrical signals.

In some embodiments, evaluating the patient's condition includes using inputs from a caregiver.

In some embodiments, evaluating the patient's condition optionally includes using personalization data associated with the patient.

In some embodiments, evaluating the patient's condition optionally includes using personalization data associated with the patient optionally provided as inputs from a caregiver.

An aspect of some embodiments includes providing an IPG which provides treatment which includes a mix of Cardiac Contractility Modulation treatment and Cardiac Resynchronization Therapy (CRT) treatment.

In some embodiments, the IPS optionally provides Cardiac Contractility Modulation treatment in cardiac cycles in which the IPG is programmed not to provide CRT pacing treatment.

In some embodiments, the IPG optionally provides Cardiac Contractility Modulation treatment in every cardiac cycle in which the IPG does not provide CRT pacing.

In some embodiments, the IPG optionally provides Cardiac Contractility Modulation treatment in some of the cardiac cycle in which the IPG does not provide CRT pacing In some embodiments, the IPG optionally provides Cardiac Contractility Modulation treatment during no more than a set time per day, for example no more than 5 hours per day.

In some embodiments, the IPG optionally provides Cardiac Contractility Modulation treatment during no more than a specific percentage of heartbeats, for example no more than 50%, 40%, 20% of the heartbeats.

In some embodiments the IPG optionally provides Cardiac Contractility Modulation treatment starting with a pulse polarity which is an opposite of the polarity of the CRT pacing. For example, when the CRT pacing uses positive pulses, the Cardiac Contractility Modulation treatment is optionally bi-phasic, and optionally starts with a negative pulse portion followed by a positive pulse portion.

It is noted that providing a negative Cardiac Contractility Modulation pulse portion following a positive CRT pacing signal potentially balances the electrical condition of the heart.

In some embodiments the IPG optionally waits for a period of time, followed by detecting a natural ventricle contraction before providing Cardiac Contractility Modulation treatment.

In some embodiments the period of time is in a range from 20-50 mS. In some embodiments the period of time is in a range from 0-100 mS, in a range from 0-50 mS, in a range from 10-50 mS, in a range from 30-40 mS.

An aspect of some embodiments includes providing an IPG which provides treatment which includes a mix of Cardiac Contractility Modulation treatment and pacemaker treatment.

In some embodiments, the mix of Cardiac Contractility Modulation treatment and pacemaker treatment is optionally used for treatment of sick sinus syndrome.

In some embodiments, Cardiac Contractility Modulation treatment is provided only in cardiac cycles which have been triggered by the pacemaker.

In some embodiments, Cardiac Contractility Modulation treatment is provided in cardiac cycles which have not been triggered by the pacemaker, for example in cardiac cycles which have been triggered by natural pacing.

In some embodiments, Cardiac Contractility Modulation treatment is provided in cardiac cycles which have not been triggered by the pacemaker, when a patient's heartbeat is in a specific range. By way of a non-limiting example, the heartbeat range is from 60 to 100 beats-per-minute, or a higher range, 100-140 beats-per-minute, or an inclusive range of 45-145 beats-per-minute.

An IPG is potentially able to analyze electric signals from a heart and determine the heartbeat within less than a heartbeat, and decide whether to provide Cardiac Contractility Modulation therapy within the same heartbeat for which the heartbeat was measured and calculated.

Figure 6A:
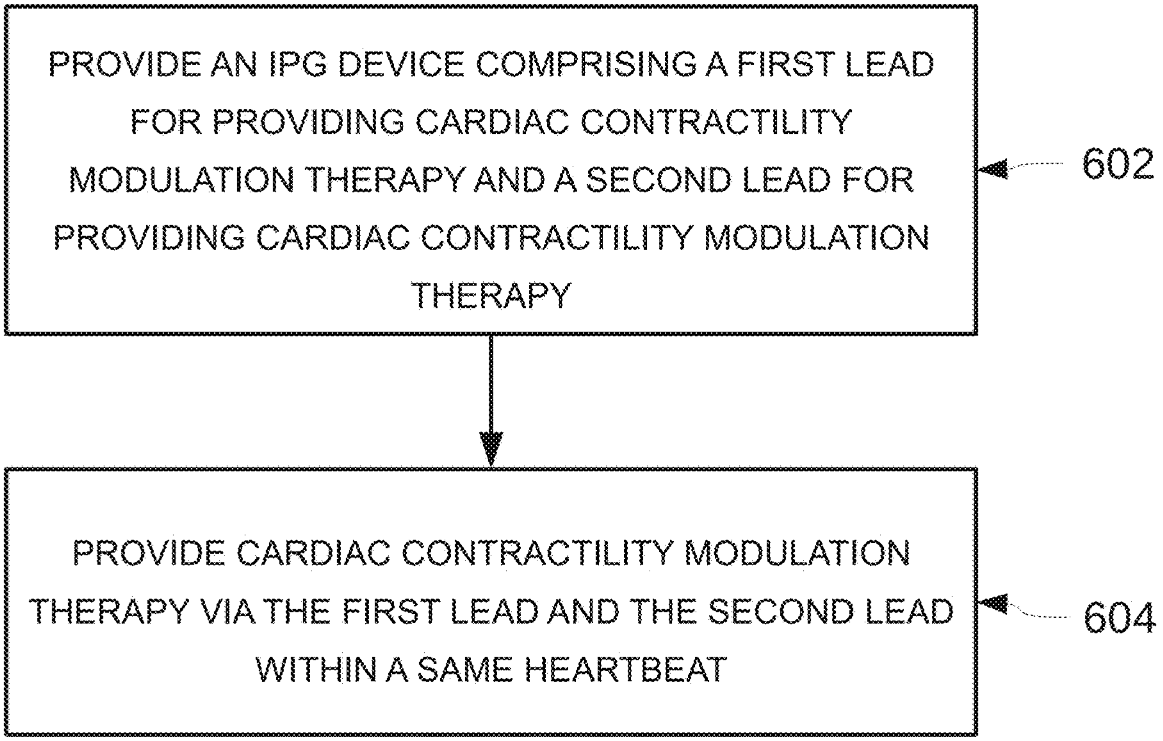
FIG. 6A is a simplified flow chart diagram of a method of providing Cardiac Contractility Modulation therapy according to an example embodiment.

Reference is now made to FIG. 6A, which is a simplified flow chart diagram of a method of providing Cardiac Contractility Modulation therapy according to an example embodiment.

The method of FIG. 6A includes:

providing an Implantable Pulse Generator (IPG) device comprising a first lead for providing Cardiac Contractility Modulation therapy and a second lead for providing Cardiac Contractility Modulation therapy (602); and providing Cardiac Contractility Modulation therapy via the first lead and the second lead within a same heartbeat (604).

Figure 6B:
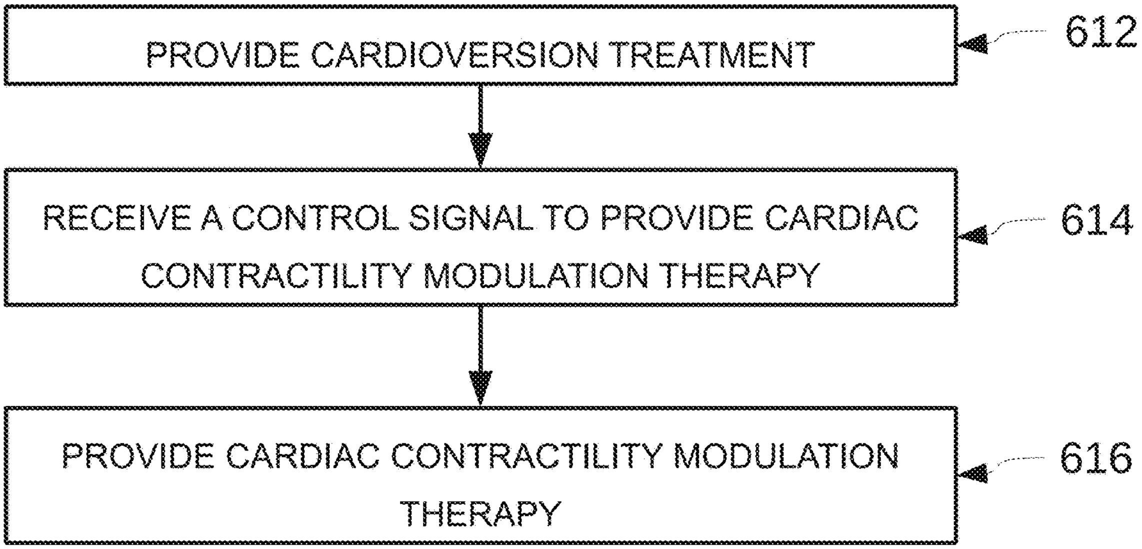
FIG. 6B is a simplified flow chart diagram of a method of providing cardiac therapy according to an example embodiment.

Reference is now made to FIG. 6B, which is a simplified flow chart diagram of a method of providing cardiac therapy according to an example embodiment.

The method of FIG. 6B includes:

providing cardioversion treatment (612);

receiving a control signal to provide Cardiac Contractility Modulation therapy (614); and providing Cardiac Contractility Modulation therapy (616).

In some embodiments, the cardioversion treatment provides a synchronized or timed signal, and the Cardiac Contractility Modulation therapy is optionally provided after the cardioversion signal, in some embodiments within a same heartbeat, and in some embodiments in a later heartbeat(s).

In some embodiments, the control signal is automatically provided from a control module, such as the control module 151 shown in FIG. 1B. In some embodiments, the control module measures a time between the cardioversion treatment and the providing Cardiac Contractility Modulation therapy.

Figure 6C:
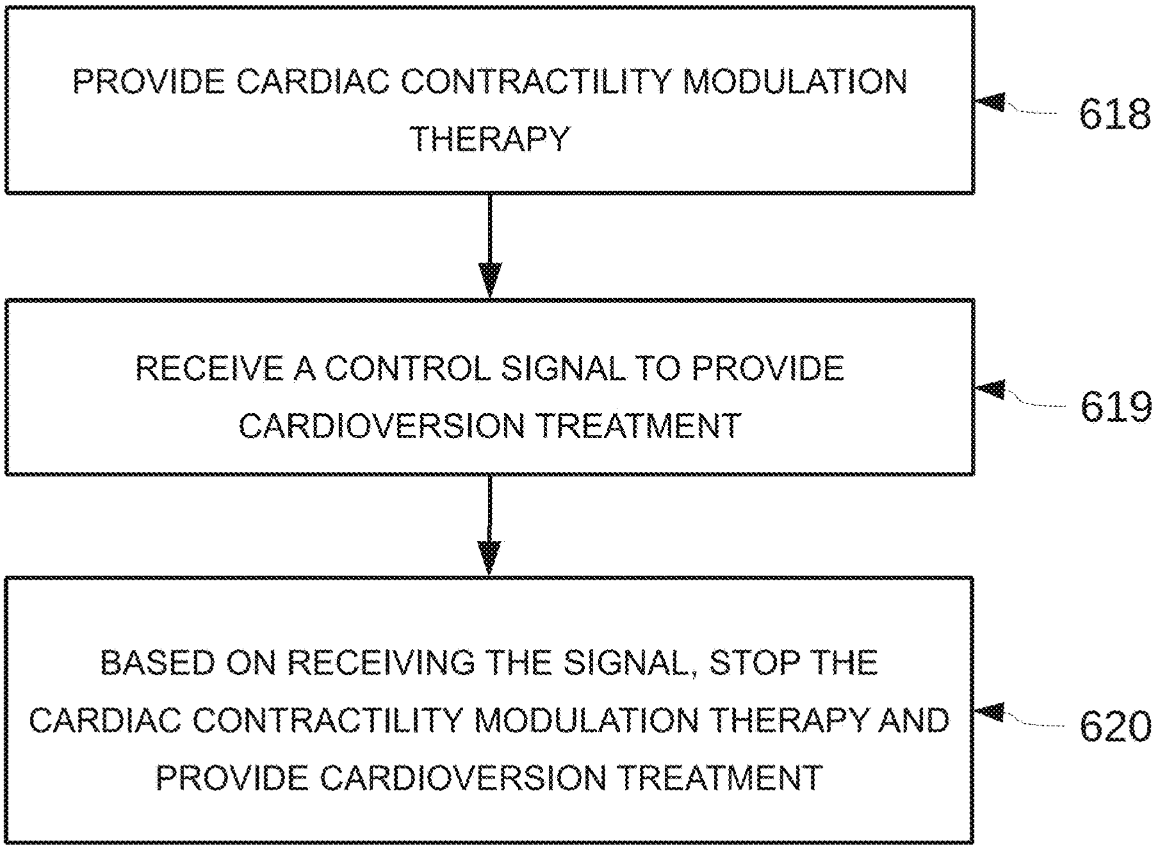
FIG. 6C is a simplified flow chart diagram of a method of providing cardiac therapy according to an example embodiment.

Reference is now made to FIG. 6C, which is a simplified flow chart diagram of a method of providing cardiac therapy according to an example embodiment.

The method of FIG. 6C includes:

providing Cardiac Contractility Modulation therapy (618);

receiving a control signal to provide cardioversion treatment (619); and based on receiving the signal, stopping the Cardiac Contractility Modulation therapy and providing cardioversion treatment (620).

Figure 6D:
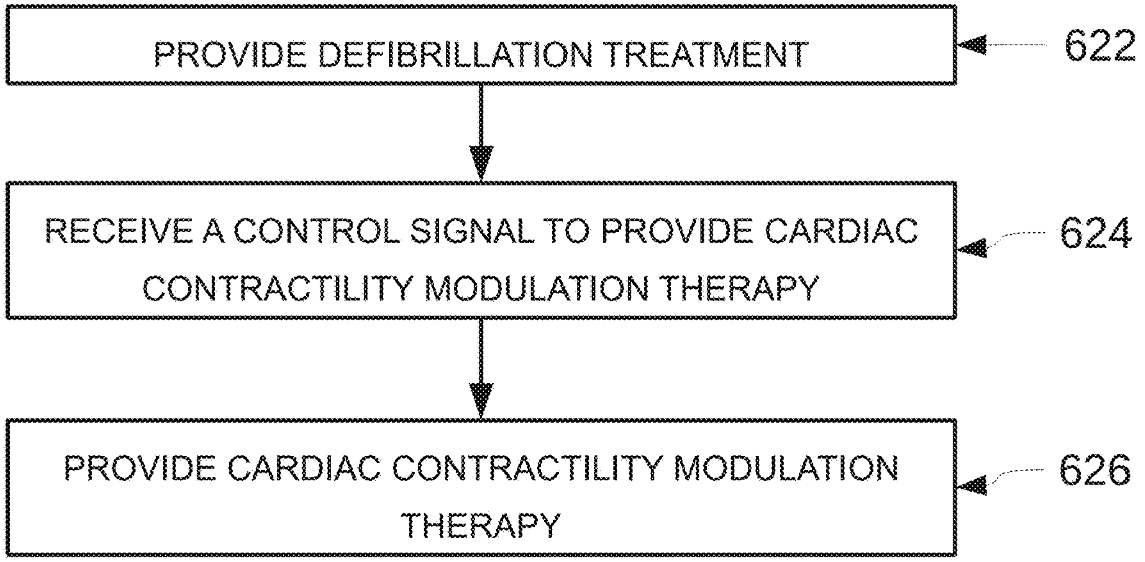
FIG. 6D is a simplified flow chart diagram of a method of providing cardiac therapy according to an example embodiment.

Reference is now made to FIG. 6D, which is a simplified flow chart diagram of a method of providing cardiac therapy according to an example embodiment.

The method of FIG. 6D includes:

providing defibrillation treatment (622);

receiving a control signal to provide Cardiac Contractility Modulation therapy (624); and providing Cardiac Contractility Modulation therapy (626).

In some embodiments, the defibrillation treatment optionally provides a non-synchronized signal, and the Cardiac Contractility Modulation therapy is optionally provided after the defibrillation signal, in a heartbeat(s) following a heartbeat during which the defibrillation signal is provided.

In some embodiments, the control signal is automatically provided from a control module, such as the control module 151 shown in FIG. 1B. In some embodiments, the control module senses if an IPG has provided defibrillation during a heartbeat, and automatically determines whether to provide the control signal to provide Cardiac Contractility Modulation therapy.

Figure 6E:
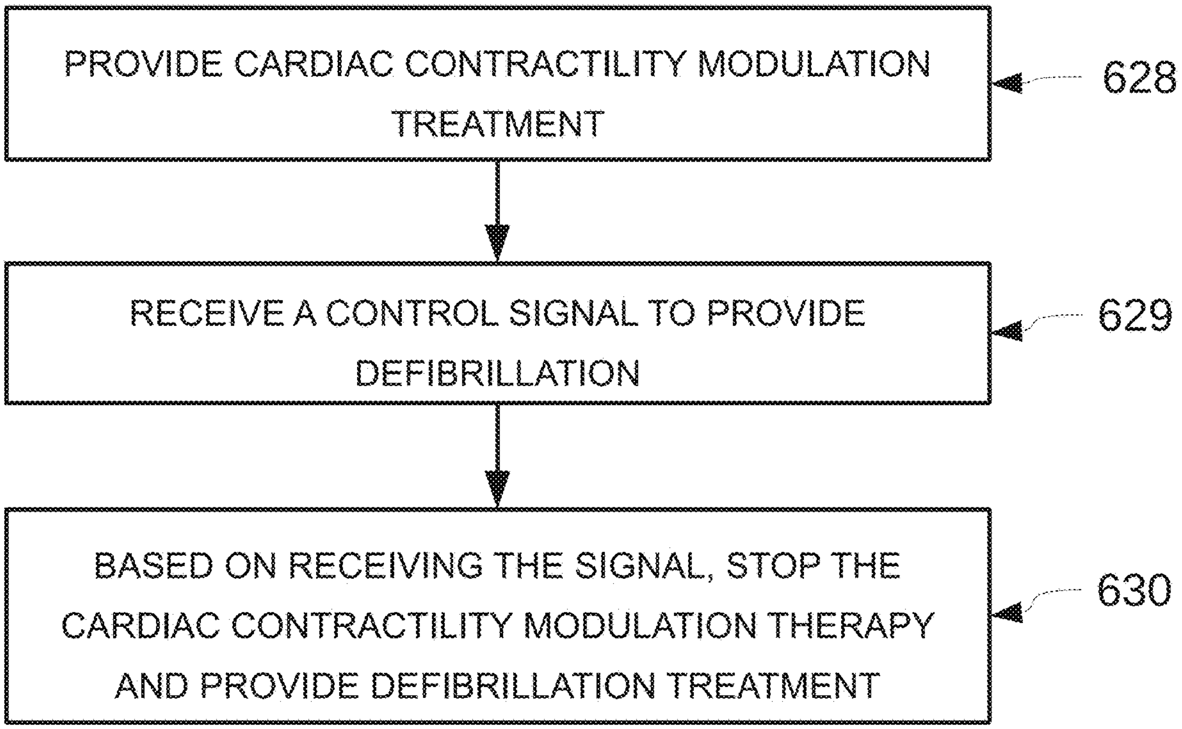
FIG. 6E is a simplified flow chart diagram of a method of providing cardiac therapy according to an example embodiment.

Reference is now made to FIG. 6E, which is a simplified flow chart diagram of a method of providing cardiac therapy according to an example embodiment.

The method of FIG. 6E includes:

providing Cardiac Contractility Modulation treatment (628);

receiving a control signal to provide defibrillation (629); and based on receiving the signal, stopping the Cardiac Contractility Modulation therapy and providing defibrillation treatment (630).

Figure 6F:
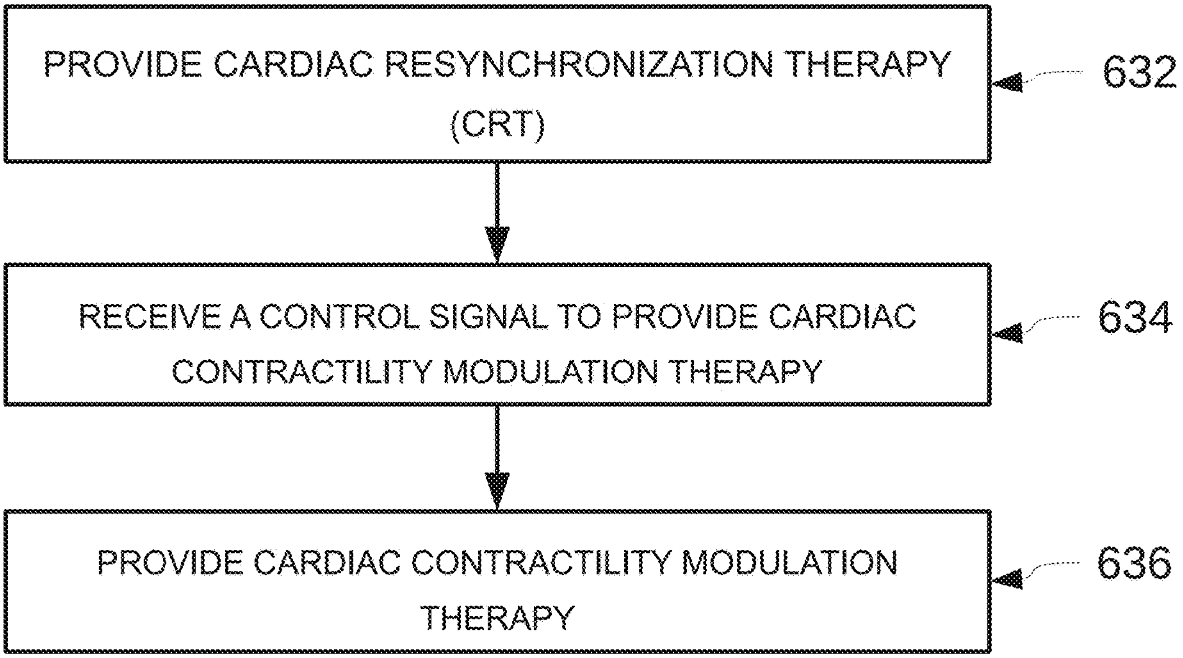
FIG. 6F is a simplified flow chart diagram of a method of providing cardiac therapy according to an example embodiment.

Reference is now made to FIG. 6F, which is a simplified flow chart diagram of a method of providing cardiac therapy according to an example embodiment.

The method of FIG. 6F includes:

providing Cardiac Resynchronization Therapy (CRT) (632);

receiving a control signal to provide Cardiac Contractility Modulation therapy (634); and providing Cardiac Contractility Modulation therapy (636).

In some embodiments, the control signal is automatically provided from a control module, such as the control module 151 shown in FIG. 1B. In some embodiments, the control module senses when an IPG has provided Cardiac Resynchronization Therapy, and automatically determines whether and/or when to provide the control signal to provide Cardiac Contractility Modulation therapy.

Figure 6G:
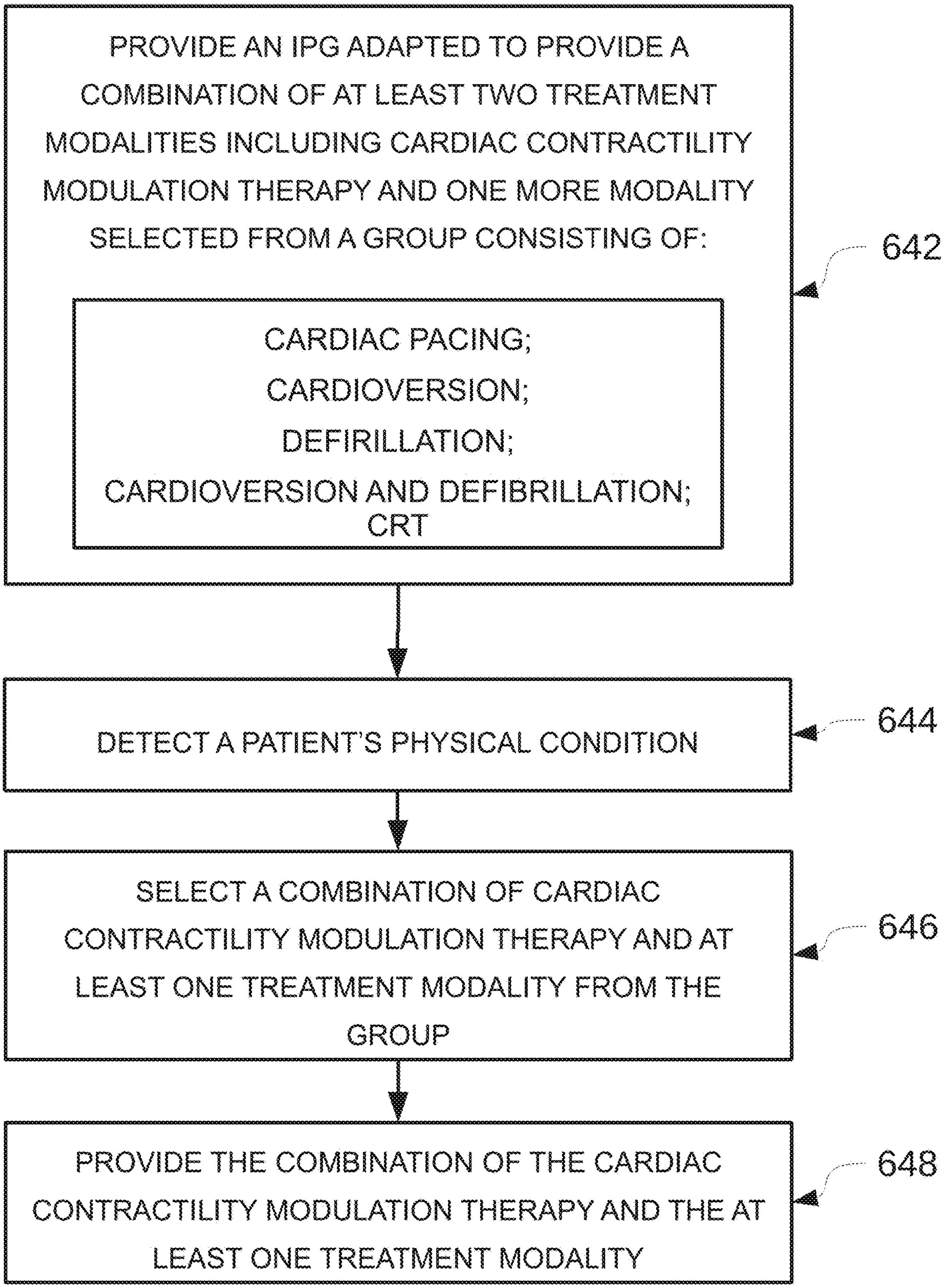
FIG. 6G is a simplified flow chart diagram of a method of treating a heart according to an example embodiment.

Reference is now made to FIG. 6G, which is a simplified flow chart diagram of a method of treating a heart according to an example embodiment.

The method of FIG. 6G includes:

providing an Implantable Pulse Generator (IPG) (642) adapted to provide a combination of at least two treatment modalities including Cardiac Contractility Modulation therapy and one more modality selected from a group consisting of:

Cardiac pacing;

Cardioversion;

Defibrillation;

Cardioversion and Defibrillation; and

Cardiac Resynchronization Therapy (CRT);

detecting a patient's physical condition (644); and selecting a combination of Cardiac Contractility Modulation therapy and at least one treatment modality from the group (646); and providing the combination of the Cardiac Contractility Modulation therapy and the at least one treatment modality (648).

Figure 6H:
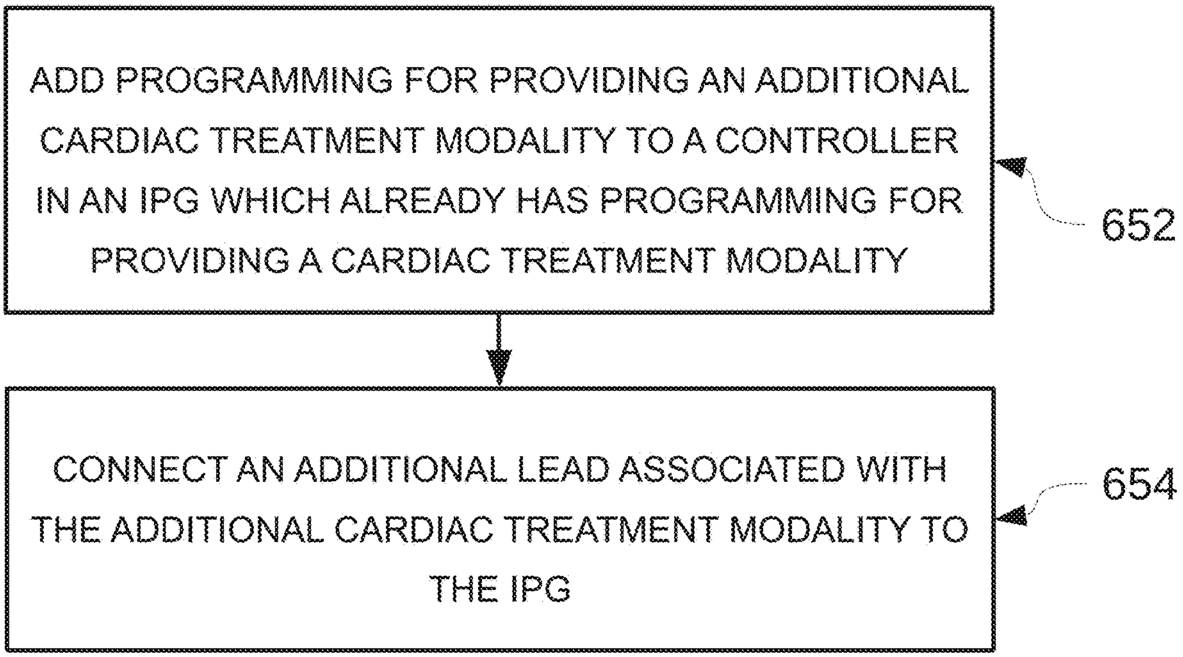
FIG. 6H is a simplified flow chart diagram of a method of adding a cardiac treatment modality to an Implantable Pulse Generator (IPG) according to an example embodiment.

Reference is now made to FIG. 6H, which is a simplified flow chart diagram of a method of adding a cardiac treatment modality to an Implantable Pulse Generator (IPG) according to an example embodiment.

The method of FIG. 6H includes:

adding programming for providing an additional cardiac treatment modality to a controller in an IPG which already has programming for providing a cardiac treatment modality (652); and connecting an additional lead associated with the additional cardiac treatment modality to the IPG (654).

IPG Measurement of Treatment Effectiveness Over an Evaluation Period

In some embodiments, an IPG optionally measures and records cardiac parameters of a patient during a specific period of time, also termed herein an evaluation period. One or more of the cardiac parameter(s) potentially reflect efficacy of one or more treatment modalities provided by the IPG over some or all of the evaluation period.

In some embodiments, the IPG uses sensing logic or algorithms which are built into various treatment modality circuitries, for example as shown in FIG. 1B or FIG. 2.

In some embodiments, the IPG optionally uses circuitry associated with various treatment modalities to sense, optionally analyze, and optionally reach a decision regarding providing the treatment, and records the decisions over some or all of the evaluation period.

In some embodiments, the blocks 202 204 205 206 208 shown in FIG. 2 may each be used separately or in parallel to sense, analyze and decide whether the treatment modality associated with the block should be provided. Optionally, the IPG may record such decisions or statistical parameters related to the decisions even when the treatment modality does not provide the pulse associated with the treatment modality.

In some embodiments, some or all of the blocks 202 204 205 206 208 shown in FIG. 2 may include a first sub-block (not shown) for sensing, analyzing and deciding whether the treatment modality associated with the block should be provided, and a second sub-block (not shown) for providing the pulse appropriate for the treatment modality.

In some embodiments, one treatment modality module, or block 202 204 205 206 208 of FIG. 2 may optionally include several algorithms for deciding whether to provide the associated treatment, and the IPG may record each one of the decisions and an associated algorithm identifier.

In some embodiments, additional hardware may be added to an IPG, such as timers and/or sensors and/or computing cores to perform multiple analyses in parallel.

By way of a non-limiting example, the defibrillation generator 205 of FIG. 2 may be used and a number of defibrillation decisions counted, with or without actually providing defibrillation pulses.

By way of another non-limiting example, the cardioversion generator 204 of FIG. 2 may be used and a number of cardioversion decisions counted, with or without actually providing defibrillation pulses.

The evaluation period typically lasts over multiple heartbeats, lasting minutes, hours, days, weeks, a month, two months, a year, or more, and cardiac parameter values reflect statistics summarizing the cardiac parameters over the evaluation period. In some embodiments, the summary may include a number of occurrences of a cardiac events, a frequency of occurrences, an average (e.g. average QRS duration), a minimum, a maximum, and so on. Storing parameter summaries potentially enables an IPG to record a patient's clinical condition within a limited memory of an IPG. Sending parameter summaries to a device external to a patient body, or to a physician, potentially provides a benefit of clinically relevant data which has been at least partially analyzed.

In some embodiments, the device external to the patient's body may include one or more of: a charger associated with the IPG, a programmer associated with the IPG, a computer in communication with the IPG.

In some embodiments, selecting and/or providing a treatment modality and/or a combination of treatment modalities is/are optionally based on information which potentially reflects clinical effectiveness of the treatment modality or treatment modalities.

In some embodiments, the IPG includes storage for one or more threshold values, associated with one or more cardiac parameters, which potentially enable the IPG to automatically select which treatment modalities are provided, and/or to assist a physician to decide.

In some embodiments, by way of a non-limiting example, a physician may enter a first arrhythmia value when instructing the IPG to perform defibrillation or ICD treatment. The IPG gather arrhythmia data over time, and a comparison of the gathered arrhythmia data to the first arrhythmia value may indicate clinical efficacy of the treatment.

In some embodiments, the IPG may optionally use the cardiac parameters recorded to automatically decide to provide one or more specific treatment modality or modalities, which may include: continuing a treatment modality, changing to a different treatment modality, adding a treatment modality to be provided in addition to a continuing treatment modality.

In some embodiments, the cardiac parameters recorded may be reported to a physician, who may decide, based on receiving the cardiac parameters collected over the evaluation period from the IPG, to provide a specific treatment modality, which may be: continuing a treatment modality, changing to a different treatment modality, adding a treatment modality to be provided in addition to a continuing treatment modality. The physician may instruct the IPG to provide the specific treatment modality.

The cardiac information gathered includes, by way of some non-limiting examples:

an arrhythmia level of a ventricle (for example measured as a number of arrhythmia occurrences per time unit);

an arrhythmia level of an atrium (for example measured as a number of arrhythmia occurrences per time unit);

a duration of the QRS complex (for example measured as one or more of an average duration, a minimal duration, a maximal duration, a standard deviation of durations per time unit);

cardiac output (for example measured as one or more of an average cardiac output, a minimal cardiac output, a maximal cardiac output, a standard deviation of cardiac output per time unit);

stroke volume (SV) (for example measured as one or more of an average SV, a minimal SV, a maximal SV, a standard deviation of SV per time unit);

end diastolic volume (EDV) (for example measured as one or more of an average EDV, a minimal EDV, a maximal EDV, a standard deviation of EDV per time unit); and an SV/EDV ratio (for example measured as one or more of an average SV/EDV ratio, a minimal SV/EDV ratio, a maximal SV/EDV ratio, a standard deviation of SV/EDV ratio per time unit).

In some embodiments, the specific period of time may be 1 day to 1 year, for example 1 month.

In some embodiments, the time unit used to store measurements and/or calculate measurement statistics per time unit may be 1 minute, 1 hour, 1 day, 1 week, 1 month to 1 year, for example 1 hour or 1 day.

In some embodiments, selection of 2 or more modalities is based on the cardiac information accumulated during the specific period of time.

In some cases the selection is done by an external operator that selects the 2 or more modalities, In some embodiments by receiving the cardiac information accumulated during the specific period of time from the IPG and assessing the cardiac information.

In some embodiments, selection of ICD treatment modality is optionally based on evaluating a patient's level of arrhythmia and/or the patient's medical history.

In some embodiments, selection of CRT modality is based on evaluation of a duration of the QRS complex and/or the patient's medical history. By way of a non-limiting example, if duration of the QRS complex is more than 120 millisecond, the IPG may initiate operation of CRT modality, or indicate to a physician desirability of operation of CRT modality.

In some embodiments, selection of Cardiac Contractility Modulation modality is optionally based on the a patient cardiac contractility level, for example based on information related to SV and/or EDV, and/or the patient's medical history.

In some cases the patient's medical history information (by way of some non-limiting examples: hypertension, history of myocardial infarct, history of ventricle arrhythmia events, history of atrial arrhythmia events, BMI, glucose level, NYHA class, ejection fraction, SV/EDV, age, gender) is sent by an operator to be stored in the device.

In some embodiments, the patient's medical history information may optionally be used for selection of 2 or more treatment modalities.

In some embodiments, medical data such as described herein, may be collected in the IPG over the specific period of time.

In some embodiments, the IPG may evaluate a clinical effect of CRT and/or Cardiac Contractility Modulation modalities and select one or 2 of the treatment modalities based on the clinical effect of the modalities over the specific period of time.

In some embodiments, the IPG optionally selects or provides a positive indication for the following modality combinations based on the following conditions:

selecting both ICD and CRT—typically used when using a Cardiac Contractility Modulation modality does not provide a clinical benefit during the evaluation period.

selecting both ICD and Cardiac Contractility Modulation—typically used when CRT modality does not provides clinical benefit during the evaluation period.

selecting all of ICD, Cardiac Contractility Modulation and CRT—typically used when both Cardiac Contractility Modulation and CRT modalities provide benefit independently or when used together during the evaluation period.

In some embodiments, the parameters measured to assess clinical benefit optionally include one or more of: cardiac output; NYHA class; quality-of-life score; average HR; and an SV/EDV ratio.

In some embodiments, the clinical benefit is optionally determined based on a value of one or more of the parameters. In some embodiments, the clinical benefit is optionally determined based on comparing a value of one or more of the parameters to a reference value stored in the IPG and associated with a treatment modality.

In some embodiments, the clinical benefit is optionally determined based on improvement of one or more of the parameters.

In some embodiments, the improvement of one or more of the parameters is considered to provide clinical benefit when occurring without deterioration of the other parameters.

In some embodiments, Cardiac Contractility Modulation is optionally selected as one of the 2 or more modalities.

In some embodiments, ICD treatment is optionally selected as one of the 2 or more modalities if a level of arrhythmia exceeds an arrhythmia threshold.

In some embodiments, ICD treatment is optionally selected as one of the 2 or more modalities if a level of ventricular arrhythmia exceeds a ventricular arrhythmia threshold.

In some embodiments, ICD treatment is optionally selected as one of the 2 or more modalities if a level of atrial arrhythmia exceeds an atrial arrhythmia threshold.

In some embodiments, CRT treatment is optionally selected as one of the 2 or more modalities if duration of QRS complex exceeds a QRS duration threshold.

In some embodiments, Cardiac Contractility Modulation treatment modality is optionally selected as one of the 2 or more modalities if SV/EDV ratio is below an SV/EDV ratio threshold.

Additional examples of IPG indications or automatic IPG treatment selection include:

Example 1 the IPG provides defibrillation treatment (ICD), and the IPG measures at least cardiac parameters associated with efficacy of the defibrillation treatment over a first evaluation period;

the IPG adds Cardiac Resynchronization Therapy (CRT) in addition to the ICD treatment, and the IPG measures at least cardiac parameters associated with efficacy of the treatment over a second evaluation period;

cardiac parameters of the first evaluation period and the second evaluation period are compared (by the IPG itself, by a charger or programmer in contact with the IPG, by a cloud program receiving data from the IPG or by a physician), and continues with one of the two above-mentioned treatments based on which treatment provided better efficacy.

Example 2

Similar to Example 1 above, with the first treatment being ICD, the second treatment being Cardiac Contractility Modulation.

Example 3 the IPG provides defibrillation treatment (ICD), and the IPG measures at least cardiac parameters associated with efficacy of the defibrillation treatment over a first evaluation period;

the IPG adds both CRT and Cardiac Contractility Modulation in addition to the ICD treatment, and the IPG measures at least cardiac parameters associated with efficacy of the treatment over a second evaluation period;

cardiac parameters of the first evaluation period and the second evaluation period are compared (by the IPG itself, by a charger or programmer in contact with the IPG, by a cloud program receiving data from the IPG or by a physician), and continues with one of the two above-mentioned treatments based on which treatment provided better efficacy.

Example 4 the IPG provides Cardiac Contractility Modulation treatment, and the IPG measures at least cardiac parameters associated with efficacy of the Cardiac Contractility Modulation treatment over a first evaluation period;

the IPG adds ICD in addition to the Cardiac Contractility Modulation treatment, and the IPG measures at least cardiac parameters associated with efficacy of the treatment over a second evaluation period;

cardiac parameters of the first evaluation period and the second evaluation period are compared (by the IPG itself, by a charger or programmer in contact with the IPG, by a cloud program receiving data from the IPG or by a physician), and continues with one of the two above-mentioned treatments based on which treatment provided better efficacy.

Example 5

Similar to Example 4 above, with the first treatment being Cardiac Contractility Modulation, the second treatment being CRT.

Example 6 the IPG provides Cardiac Contractility Modulation, and the IPG measures at least cardiac parameters associated with efficacy of the treatment over a first evaluation period;

the IPG adds both ICD and CRT in addition to the Cardiac Contractility Modulation treatment, and the IPG measures at least cardiac parameters associated with efficacy of the treatment over a second evaluation period;

cardiac parameters of the first evaluation period and the second evaluation period are compared (by the IPG itself, by a charger or programmer in contact with the IPG, by a cloud program receiving data from the IPG or by a physician), and continues with one of the two above-mentioned treatments based on which treatment provided better efficacy.

Example 7 the IPG provides Cardiac Contractility Modulation treatment, and the IPG measures at least cardiac parameters associated with efficacy of the Cardiac Contractility Modulation treatment over a first evaluation period;

if an arrhythmia related cardiac parameter is found to be higher than a threshold value, the the IPG itself, or a charger or programmer in contact with the IPG, or a cloud program receiving data from the IPG, or a physician, provide an indication and/or an instruction to add ICD treatment in addition to the CCM treatment.

Example 8 the IPG provides Cardiac Contractility Modulation treatment, and the IPG measures at least cardiac parameters associated with efficacy of the Cardiac Contractility Modulation treatment over a first evaluation period;

if a duration of a QRS complex related parameter is found to be longer than a threshold value, the the IPG itself, or a charger or programmer in contact with the IPG, or a cloud program receiving data from the IPG, or a physician, provide an indication and/or an instruction to add CRT treatment in addition to the CCM treatment.

It is noted, and described above, that in some embodiments the IPG optionally enables:

programming a series of treatments and combinations of treatments;

measuring cardiac parameters during evaluation periods associated with the treatments; and comparing the cardiac parameters associated with the treatments.

In some embodiments, the above may be followed by a suggestion by the IPG of a treatment or combination of treatments which potentially provides most benefit to the patient, based on the patient's cardiac parameters obtained during the series.

In some embodiments, the above may be followed by a selection (by the IPG or by a physician), of a treatment or combination of treatments which provide most benefit to the patient, based on the patient's cardiac parameters obtained during the series.

In some embodiments, a physician optionally communicates with the IPG, via a programmer or charger or control device, or via other forms of communication, and provides data such as which treatment sequences to provide, a duration of their provision, and thresholds which may provide indications for changes in treatment, and even actual changes in the treatment.

It is expected that during the life of a patent maturing from this application many relevant IPGs will be developed and the scope of the term IPG is intended to include all such new technologies a priori.

As used herein with reference to quantity or value, the term "about" means "within ±25% of".

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety

What is claimed is:

1. An Implantable Pulse Generator (IPG) comprising:

Cardiac Contractility Modulation generator circuitry adapted to provide a Cardiac Contractility Modulation treatment modality;

pacing generator circuitry adapted to provide a cardiac pacing treatment modality;

Cardioversion generator circuitry adapted to provide a Cardioversion treatment modality;

defibrillation pulse generator circuitry adapted to provide a Defibrillation treatment modality;

Cardiac Resynchronization Therapy (CRT) generator circuitry adapted to provide a Cardiac Resynchronization Therapy (CRT) treatment modality; and a controller adapted to gather cardiac data to evaluate clinical benefit of providing at least one of the treatment modalities over an evaluation period which lasts plurality of hours; wherein the IPG is enabled to determine the clinical benefit by comparing at least some of the cardiac data to reference data comprised in the IPG;

wherein the controller is configured to provide a specific treatment modality based on said evaluated clinical benefit and stored cardiac parameter values.

2. An IPG according to claim 1 wherein the IPG includes storage for storing said value of the clinical benefit.

3. An IPG according to claim 1 wherein the controller is adapted to perform one or more of the following:

a. record a decisions associated with one or more of the Cardiac Contractility Modulation generator circuitry, the pacing generator circuitry, the Cardioversion generator circuitry, the defibrillation pulse generator circuitry, and the CRT generator circuitry, even when the circuitries do not provide pulse activation;

b. detect a decline in clinical benefit of a treatment modality.

4. An IPG according to claim 3, wherein said decision is regarding providing treatment modality from said one or more circuitries.

5. An IPG according to claim 1 wherein the controller is adapted to provide one of the following:

a. a combination of said Defibrillation and CRT treatment modalities if providing the Cardiac Contractility Modulation treatment modality has not provided clinical benefit over the evaluation period;

b. a combination of said Defibrillation and Cardiac Contractility Modulation treatment modalities if providing the CRT treatment modality has not provided clinical benefit over the evaluation period;

c. a combination of said Defibrillation, Cardiac Contractility Modulation, and CRT treatment modalities if providing the Cardiac Contractility Modulation and CRT treatment modalities have provided clinical benefit over the evaluation period.

6. An IPG according to claim 1, wherein the controller is programmable to:

provide a series of treatment modalities and combinations of treatment modalities;

measure cardiac parameters during evaluation periods associated with the treatment modalities;

compare the cardiac parameters associated with the treatment modalities; and select a treatment modality or combination of treatment modalities based on the patient's cardiac parameters obtained during the series.

7. An IPG according to claim 1 configured, using sensors comprised in the IPG, to measure one or more cardiac parameter(s) selected from a group consisting of:

a level of ventricle arrhythmia;

a level of atrial arrhythmia;

a duration of a QRS complex;

cardiac output (CO);

stroke volume (SV); and end diastolic volume (EDV), and store data associated with the cardiac parameter over said evaluation period.

8. An IPG according to claim 1 wherein said evaluation period lasts at least one day.

9. An IPG according to claim 7 wherein the controller is adapted to perform one or more of the following:

a. provide ICD treatment modality if level of ventricular arrhythmia exceed a ventricular arrhythmia threshold;

b. provide CRT treatment modality if duration of QRS complex exceeds a QRS duration threshold;

c. provide Cardiac Contractility Modulation treatment modality if SV/EDV ratio is below an SV/EDV ratio threshold;

d. control the IPG and the generator circuitry to switch between providing one of the treatment modalities and another of the treatment modalities.

10. An IPG according to claim 1, wherein the IPG comprises leads sized for reaching locations where the treatment modalities are to be provided.

11. An IPG according to claim 1, wherein the IPG is adapted to perform one of the following:

a. select which two of the treatment modalities is to be provided;

b. select providing Cardiac Contractility Modulation and one other of the treatment modalities;

c. provide all of the treatment modalities; or d. record a patient's clinical condition status and send said status to a device external to a patient body.

12. An IPG according to claim 1, the IPG comprising one of the following:

a. a first lead for providing Cardiac Contractility Modulation therapy;

a second lead for providing Cardiac Contractility Modulation therapy; and a therapy controller adapted to control provide Contractility Modulation therapy via the first lead and the second lead within a same heartbeat, wherein the device is adapted to provide a different pattern of Cardiac Contractility Modulation pulses via the first lead than via the second lead;

b. a first lead shaped and configured for providing Cardiac Contractility Modulation therapy to a right ventricle;

a second lead shaped and configured for providing Cardiac Contractility Modulation therapy to the right ventricle;

a third lead shaped for placing in a right atrium; and a controller adapted to switch providing between at least two treatment modalities selected from a group consisting of:

Cardiac Contractility Modulation;

Cardiac pacing;

Cardioversion;

Defibrillation;

Cardioversion and Defibrillation, and

Cardiac Resynchronization Therapy (CRT), the controller adapted to control provide Contractility Modulation therapy via the first lead and the second lead within a same heartbeat.

13. An IPG according to claim 12, wherein at least one of the leads comprises a shock coil and a pacing electrode in the lead;

wherein the device is adapted to provide a pacing signal through the first lead to the right ventricle and through the third lead to the right atrium within a same heartbeat.

14. An IPG according to claim 1, wherein said defibrillation pulse generator circuitry is comprised in an implantable cardioverter defibrillation (ICD).

15. An IPG according to claim 1, wherein the controller is adapted to switch providing between at least two treatment modalities selected from a group consisting of Cardiac Contractility Modulation, Cardiac pacing, Cardioversion, Defibrillation, Cardioversion and Defibrillation, and Cardiac Resynchronization Therapy (CRT).

16. An IPG according to claim 1, wherein cardiac parameter values of said cardiac data reflect statistics summarizing the cardiac parameter values over said evaluation period.

17. A method of treating a heart, the method comprising:

providing an Implantable Pulse Generator (IPG) adapted to provide a combination of at least two treatment modalities including Cardiac Contractility Modulation therapy and one more modality selected from a group consisting of:

Cardiac pacing;

Cardioversion;

Defibrillation;

Cardioversion and Defibrillation; and

Cardiac Resynchronization Therapy (CRT);

detecting a patient's physical condition; and selecting a combination of two or more treatment modalities from the group based on cardiac parameters gathered over an evaluation period which lasts plurality of hours; and providing the two or more treatment modalities.

18. A method according to claim 17 comprising providing one of the following:

a. a combination of Cardioversion and Defibrillation with CRT treatment modalities if providing the Cardiac Contractility Modulation treatment modality has not provided clinical benefit over the evaluation period;

b. a combination of Cardioversion and Defibrillation with Cardiac Contractility Modulation treatment modalities if providing the CRT treatment modality has not provided clinical benefit over the evaluation period;

c. a combination of Cardioversion and Defibrillation, Cardiac Contractility Modulation, and CRT treatment modalities if providing the Cardiac Contractility Modulation and CRT treatment modalities have provided clinical benefit over the evaluation period;

wherein the evaluation period is at least one day.

19. A method according to claim 17, wherein providing the combination comprises refraining from providing Cardiac Contractility Modulation therapy during the same cardiac cycle in which at least one other treatment modality is provided.

20. A method according to claim 17, wherein the detecting the patient's physical condition is performed in one or more of the following manners:

a. based on a clinical parameter based on analysis of a physiological measure selected from a group consisting of:

blood pressure;
an electrocardiogram (ECG) signal;
breathing rate;
ejection fraction;
arrhythmia;
bio impedance;
a blood test;
cardiac imaging;
physical examination; and
biopsy;

b. using clinical parameters provided by a physician or by sensors comprised in the IPG.

21. A method according to claim 17 comprising using sensors comprised in the IPG measuring one or more cardiac parameter(s) selected from a group consisting of:

a level of ventricle arrhythmia;
a level of atrial arrhythmia;
a duration of a QRS complex;
cardiac output;
stroke volume (SV); and
end diastolic volume (EDV), and store data associated with the cardiac parameter(s) over said evaluation period;

wherein the evaluation period lasts at least one month.

22. A method according to claim 17 wherein the selecting comprises one or more of the following:

a. selecting ICD treatment modality if a level of ventricular arrhythmia exceed a ventricular arrhythmia threshold;

b. selecting CRT treatment modality if duration of QRS complex exceeds a QRS duration threshold;

c. selecting Cardiac Contractility Modulation treatment modality if an SV/EDV ratio is below an SV/EDV ratio threshold.

23. A method according to claim 17, wherein the IPG is used for providing defibrillation treatment; and following the providing defibrillation treatment, refraining from providing Cardiac Contractility Modulation treatment until an arrhythmia rate is below a specific threshold;

wherein the specific threshold of the arrhythmia rate is pre-programmed in the IPG.

24. A method according to claim 17, wherein the IPG is used to do one of the following:

a. provide defibrillation treatment; and following the providing defibrillation treatment, refraining from providing Cardiac Contractility Modulation treatment for a pre-programmed time period;

b. provide Cardiac Contractility Modulation treatment only in a cardiac cycle triggered by a pacemaker or CRT pulse;

c. provide Cardiac Contractility Modulation treatment only in a cardiac cycle which is not triggered by a pacemaker or CRT pulse.

* * * * *